(12) United States Patent
Khedkar et al.

(10) Patent No.: US 9,241,908 B2
(45) Date of Patent: Jan. 26, 2016

(54) ORALLY ADMINISTRABLE SOLID PHARMACEUTICAL COMPOSITION AND A PROCESS THEREOF

(75) Inventors: Anand Khedkar, Karnataka (IN); Sharath Kumar Mallapura Rangappa, Karnataka (IN); Ramesh Subramani, Tamil Nadu (IN); Nitesh Dave, Karnataka (IN); Devesh Radhakrishnan, Maharashtra (IN); Sundaresh Shankar, Karnataka (IN); Sudheer Chivukula, Karnataka (IN); Ranjith Ramakrishna, Karnataka (IN); Shanmugam Thandava Murthy, Tamil Nadu (IN); Harish Venkatraman Pai, Karnataka (IN); Nilanjan Sengupta, Karnataka (IN); Ramakrishnan Melarkode, Karnataka (IN); Harish Iyer, Karnataka (IN)

(73) Assignee: BIOCON LIMITED (IN)

( * ) Notice: Subject to any disclaimer, the term of this patent is extended or adjusted under 35 U.S.C. 154(b) by 556 days.

(21) Appl. No.: 12/682,825

(22) PCT Filed: Oct. 16, 2008

(86) PCT No.: PCT/IN2008/000683
§ 371 (c)(1),
(2), (4) Date: Apr. 13, 2010

(87) PCT Pub. No.: WO2009/050738
PCT Pub. Date: Apr. 23, 2009

(65) Prior Publication Data
US 2010/0285143 A1 Nov. 11, 2010

(30) Foreign Application Priority Data

Oct. 16, 2007 (IN) .......................... 02340/CHE/2007
Mar. 24, 2008 (IN) .......................... 00714/CHE/2008

(51) Int. Cl.
*A61K 9/20* (2006.01)
*A61K 9/16* (2006.01)
*A61K 38/28* (2006.01)
*A61K 47/48* (2006.01)

(52) U.S. Cl.
CPC ............. *A61K 9/2077* (2013.01); *A61K 9/1617* (2013.01); *A61K 9/2013* (2013.01); *A61K 9/2018* (2013.01); *A61K 9/2054* (2013.01); *A61K 38/28* (2013.01); *A61K 47/48038* (2013.01); *A61K 47/48046* (2013.01)

(58) Field of Classification Search
None
See application file for complete search history.

(56) References Cited

U.S. PATENT DOCUMENTS

| | | |
|---|---|---|
| 2,626,228 A | 1/1953 | Petersen |
| 2,789,080 A | 4/1957 | Christensen |
| 2,799,622 A | 7/1957 | Schlichtkrull et al. |
| 2,819,999 A | 1/1958 | Schlichtkrull et al. |
| 2,849,370 A | 8/1958 | Petersen et al. |
| 2,882,203 A | 4/1959 | Petersen et al. |
| 2,920,014 A | 1/1960 | Petersen et al. |
| 3,014,842 A | 12/1961 | Schlichtkrull |
| 3,058,885 A | 10/1962 | Schlichtkrull |
| 3,060,093 A | 10/1962 | Poulsen et al. |
| 3,091,573 A | 5/1963 | Schlichtkrull |
| 3,102,077 A | 8/1963 | Christensen |
| 3,256,153 A | 6/1966 | Heimlick |
| 3,868,356 A | 2/1975 | Smyth |
| 3,919,411 A | 11/1975 | Glass et al. |
| 3,950,517 A | 4/1976 | Lindsay et al. |
| 4,003,792 A | 1/1977 | Mill et al. |
| 4,044,196 A | 8/1977 | Huper et al. |
| 4,087,390 A | 5/1978 | Shields |
| 4,093,574 A | 6/1978 | Shields |
| 4,100,117 A | 7/1978 | Shields |
| 4,179,337 A | 12/1979 | Davis et al. |
| 4,223,163 A | 9/1980 | Guilloty |

(Continued)

FOREIGN PATENT DOCUMENTS

| | | |
|---|---|---|
| EP | 0 031 567 | 7/1981 |
| EP | 0 511 903 | 10/1996 |

(Continued)

OTHER PUBLICATIONS

Garber AJ, "Pharmacologic Modifications of Hormones to Improve their Therapeutic Potential for Diabetes Management"; Diabetes, Obesity and Metabolism, 2005, vol. 7, pp. 666-674.

(Continued)

*Primary Examiner* — Susan Tran
(74) *Attorney, Agent, or Firm* — Marianne Fuierer; Moore & Van Allen, PLLC

(57) ABSTRACT

The invention relates to improvised pharmaceutical compositions permitting ingestion via oral delivery of proteins/peptides or their conjugates, and/or cation-insulin conjugate complexes demonstrating desirable pharmacokinetic profiles and potency in efficacy models of diabetes in dogs and humans. A preferred formulation comprises 0.01%-20% w/w of insulin, insulin compound conjugates and/or cation insulin conjugates, 10%-60% w/w of one or more fatty acid components selected from saturated or unsaturated C4-C12 fatty acids and/or salts of such fatty acids and additionally contains optimal amounts of other pharmaceutically suitable polymer excipients which permit improved solubility, dissolution rate and effective bioavailability of poorly water soluble compositions and consistent in-vivo release profiles upon scalability during manufacture. A further aspect of the invention features the process of preparing the aforesaid formulations.

29 Claims, 16 Drawing Sheets

(56) References Cited

U.S. PATENT DOCUMENTS

| | | |
|---|---|---|
| 4,229,438 A | 10/1980 | Fujino et al. |
| 4,253,998 A | 3/1981 | Sarantakis |
| 4,277,394 A | 7/1981 | Fujino et al. |
| 4,338,306 A | 7/1982 | Kitao et al. |
| 4,348,387 A | 9/1982 | Brownlee et al. |
| 4,410,547 A | 10/1983 | Ueno et al. |
| 4,469,681 A | 9/1984 | Brownlee et al. |
| 4,472,382 A | 9/1984 | Labrie et al. |
| 4,476,113 A | 10/1984 | Young et al. |
| 4,554,101 A | 11/1985 | Hopp |
| 4,579,730 A | 4/1986 | Kidron et al. |
| 4,585,745 A | 4/1986 | Tunooka et al. |
| 4,602,043 A | 7/1986 | Geho |
| 4,622,392 A | 11/1986 | Hong et al. |
| 4,654,324 A | 3/1987 | Chance et al. |
| 4,662,872 A | 5/1987 | Cane |
| 4,684,524 A | 8/1987 | Eckenhoff et al. |
| 4,698,264 A | 10/1987 | Steinke |
| 4,704,394 A | 11/1987 | Geho |
| 4,717,566 A | 1/1988 | Eckenhoff et al. |
| 4,744,976 A | 5/1988 | Snipes et al. |
| 4,761,287 A | 8/1988 | Geho |
| 4,764,592 A | 8/1988 | Massey et al. |
| 4,772,471 A | 9/1988 | Vanlerberghe et al. |
| 4,797,288 A | 1/1989 | Sharma et al. |
| 4,801,575 A | 1/1989 | Pardridge |
| 4,822,337 A | 4/1989 | Newhouse et al. |
| 4,835,142 A | 5/1989 | Suzuki et al. |
| 4,839,341 A | 6/1989 | Massey et al. |
| 4,840,799 A | 6/1989 | Appelgren et al. |
| 4,849,405 A | 7/1989 | Ecanow |
| 4,863,896 A | 9/1989 | Geho et al. |
| 4,917,888 A | 4/1990 | Katre et al. |
| 4,935,246 A | 6/1990 | Ahrens |
| 4,946,828 A | 8/1990 | Markussen |
| 4,957,910 A | 9/1990 | Sutton et al. |
| 4,963,367 A | 10/1990 | Ecanow |
| 4,963,526 A | 10/1990 | Ecanow |
| 4,994,439 A | 2/1991 | Longenecker et al. |
| 5,013,556 A | 5/1991 | Woodle et al. |
| 5,034,415 A | 7/1991 | Rubin |
| 5,055,300 A | 10/1991 | Gupta |
| 5,055,304 A | 10/1991 | Makino et al. |
| 5,089,261 A | 2/1992 | Nitecki et al. |
| 5,093,198 A | 3/1992 | Speaker et al. |
| 5,157,021 A | 10/1992 | Balschmidt et al. |
| 5,162,430 A | 11/1992 | Rhee et al. |
| 5,164,366 A | 11/1992 | Balschmidt et al. |
| 5,177,058 A | 1/1993 | Dorschug |
| 5,202,415 A | 4/1993 | Jonassen et al. |
| 5,206,219 A | 4/1993 | Desai |
| 5,283,236 A | 2/1994 | Chiou |
| 5,286,637 A | 2/1994 | Veronese et al. |
| 5,292,802 A | 3/1994 | Rhee et al. |
| 5,298,410 A | 3/1994 | Phillips et al. |
| 5,304,473 A | 4/1994 | Belagaje et al. |
| 5,308,889 A | 5/1994 | Rhee et al. |
| 5,312,808 A | 5/1994 | Shorr et al. |
| 5,320,094 A | 6/1994 | Laube et al. |
| 5,321,009 A | 6/1994 | Baeder et al. |
| 5,324,775 A | 6/1994 | Rhee et al. |
| 5,328,955 A | 7/1994 | Rhee et al. |
| 5,349,052 A | 9/1994 | Delgado et al. |
| 5,359,030 A | 10/1994 | Ekwuribe |
| 5,364,838 A | 11/1994 | Rubsamen |
| 5,405,621 A | 4/1995 | Sipos |
| 5,405,877 A | 4/1995 | Greenwald et al. |
| 5,413,791 A | 5/1995 | Rhee et al. |
| 5,415,872 A | 5/1995 | Sipos |
| 5,420,108 A | 5/1995 | Shohet |
| 5,438,040 A | 8/1995 | Ekwuribe |
| 5,444,041 A | 8/1995 | Owen et al. |
| 5,445,832 A | 8/1995 | Orsolini et al. |
| 5,446,091 A | 8/1995 | Rhee et al. |
| 5,457,066 A | 10/1995 | Frank et al. |
| 5,461,031 A | 10/1995 | De Felippis |
| 5,468,478 A | 11/1995 | Saifer et al. |
| 5,468,727 A | 11/1995 | Phillips et al. |
| 5,474,978 A | 12/1995 | Bakaysa et al. |
| 5,504,188 A | 4/1996 | Baker et al. |
| 5,506,203 A | 4/1996 | Backstrom et al. |
| 5,518,998 A | 5/1996 | Backstrom et al. |
| 5,523,348 A | 6/1996 | Rhee et al. |
| 5,529,915 A | 6/1996 | Phillips et al. |
| 5,534,488 A | 7/1996 | Hoffmann |
| 5,545,618 A | 8/1996 | Buckley et al. |
| 5,550,188 A | 8/1996 | Rhee et al. |
| 5,567,422 A | 10/1996 | Greenwald |
| 5,597,797 A | 1/1997 | Clark |
| 5,606,038 A | 2/1997 | Regen |
| 5,612,460 A | 3/1997 | Zalipsky |
| 5,631,347 A | 5/1997 | Baker et al. |
| 5,637,749 A | 6/1997 | Greenwald |
| 5,643,575 A | 7/1997 | Martinez et al. |
| 5,646,242 A | 7/1997 | Baker et al. |
| 5,650,388 A | 7/1997 | Shorr et al. |
| 5,650,486 A | 7/1997 | De Felippis |
| 5,658,878 A | 8/1997 | Backstrom et al. |
| 5,681,567 A | 10/1997 | Martinez et al. |
| 5,681,811 A | 10/1997 | Ekwuribe |
| 5,693,609 A | 12/1997 | Baker et al. |
| 5,693,769 A | 12/1997 | Kahne et al. |
| 5,700,904 A | 12/1997 | Baker et al. |
| 5,704,910 A | 1/1998 | Humes |
| 5,707,648 A | 1/1998 | Yiv |
| 5,714,519 A | 2/1998 | Cincotta et al. |
| 5,738,846 A | 4/1998 | Greenwald et al. |
| 5,747,445 A | 5/1998 | Backstrom et al. |
| 5,747,642 A | 5/1998 | De Felippis |
| 5,750,497 A | 5/1998 | Havelund et al. |
| 5,763,396 A | 6/1998 | Weiner et al. |
| 5,766,620 A | 6/1998 | Heiber et al. |
| 5,773,581 A | 6/1998 | Camble et al. |
| 5,824,638 A | 10/1998 | Burnside et al. |
| 5,830,853 A | 11/1998 | Backstrom et al. |
| 5,830,918 A | 11/1998 | Sportsman et al. |
| 5,843,866 A | 12/1998 | Parker et al. |
| 5,849,860 A | 12/1998 | Hakimi et al. |
| 5,853,748 A | 12/1998 | New |
| 5,854,208 A | 12/1998 | Jones et al. |
| 5,856,451 A | 1/1999 | Olsen et al. |
| 5,866,538 A | 2/1999 | Norup et al. |
| 5,866,584 A | 2/1999 | Cincotta et al. |
| 5,874,111 A | 2/1999 | Maitra et al. |
| 5,889,153 A | 3/1999 | Suzuki et al. |
| 5,898,028 A | 4/1999 | Jensen et al. |
| 5,902,588 A | 5/1999 | Greenwald et al. |
| 5,905,140 A | 5/1999 | Hansen |
| 5,907,030 A | 5/1999 | Shen et al. |
| 5,922,675 A | 7/1999 | Baker et al. |
| 5,932,462 A | 8/1999 | Harris et al. |
| 5,939,380 A | 8/1999 | Wang |
| 5,942,248 A | 8/1999 | Barnwell |
| 5,948,751 A | 9/1999 | Kimer et al. |
| 5,952,008 A | 9/1999 | Backstrom et al. |
| 5,952,297 A | 9/1999 | De Felippis et al. |
| 5,952,461 A | 9/1999 | Kim et al. |
| 5,955,459 A | 9/1999 | Bradley et al. |
| 5,962,267 A | 10/1999 | Shin et al. |
| 5,968,549 A | 10/1999 | New et al. |
| 5,969,040 A | 10/1999 | Hallahan et al. |
| 5,981,709 A | 11/1999 | Greenwald et al. |
| 5,985,263 A | 11/1999 | Lee et al. |
| 5,997,848 A | 12/1999 | Patton et al. |
| 6,004,574 A | 12/1999 | Backstrom et al. |
| 6,011,008 A | 1/2000 | Domb et al. |
| 6,025,325 A | 2/2000 | Campfield et al. |
| 6,034,054 A | 3/2000 | DeFelippis et al. |
| 6,042,822 A | 3/2000 | Gilbert et al. |
| 6,043,214 A | 3/2000 | Jensen et al. |
| 6,051,551 A | 4/2000 | Hughes et al. |
| 6,057,292 A | 5/2000 | Cunningham et al. |
| 6,063,761 A | 5/2000 | Jones et al. |
| 6,068,993 A | 5/2000 | Filho et al. |

(56) References Cited

U.S. PATENT DOCUMENTS

| | | | |
|---|---|---|---|
| 6,093,391 | A | 7/2000 | Kabanov et al. |
| 6,103,269 | A | 8/2000 | Wunderlich et al. |
| 6,113,906 | A | 9/2000 | Greenwald et al. |
| 6,147,108 | A | 11/2000 | Hauptman |
| 6,165,976 | A | 12/2000 | Backstrom et al. |
| 6,174,856 | B1 | 1/2001 | Langballe et al. |
| 6,177,087 | B1 | 1/2001 | Greenwald et al. |
| 6,180,599 | B1 | 1/2001 | Min |
| 6,191,105 | B1 | 2/2001 | Ekwuribe et al. |
| 6,192,887 | B1 | 2/2001 | Howett et al. |
| 6,200,602 | B1 | 3/2001 | Watts et al. |
| 6,211,144 | B1 | 4/2001 | Havelund |
| 6,221,837 | B1 | 4/2001 | Ertl et al. |
| 6,248,363 | B1 | 6/2001 | Patel et al. |
| 6,251,856 | B1 | 6/2001 | Markussen et al. |
| 6,258,377 | B1 | 7/2001 | New et al. |
| 6,268,335 | B1 | 7/2001 | Brader |
| 6,268,355 | B1 | 7/2001 | Mizobuchi et al. |
| 6,306,440 | B1 | 10/2001 | Backstrom et al. |
| 6,309,633 | B1 | 10/2001 | Ekwuribe et al. |
| 6,310,038 | B1 | 10/2001 | Havelund |
| 6,323,311 | B1 | 11/2001 | Liu et al. |
| 6,335,316 | B1 | 1/2002 | Hughes et al. |
| 6,342,225 | B1 | 1/2002 | Jones et al. |
| 6,444,641 | B1 | 9/2002 | Flora |
| 6,451,970 | B1 | 9/2002 | Schaffer et al. |
| 6,451,974 | B1 | 9/2002 | Hansen |
| 6,465,426 | B2 | 10/2002 | Brader |
| RE37,971 | E | 1/2003 | Baker et al. |
| 6,506,730 | B1 | 1/2003 | Lee et al. |
| 6,531,448 | B1 | 3/2003 | Brader |
| 6,551,992 | B1 | 4/2003 | DeFelippis et al. |
| 6,566,490 | B1 | 5/2003 | Manique et al. |
| 6,620,780 | B2 | 9/2003 | Markussen et al. |
| 6,630,157 | B1 | 10/2003 | Horrobin et al. |
| 6,652,885 | B2 | 11/2003 | Steiner et al. |
| 6,685,967 | B1 | 2/2004 | Patton et al. |
| 6,686,177 | B1 | 2/2004 | Ertl et al. |
| 6,706,289 | B2 | 3/2004 | Lewis |
| 6,726,932 | B2 | 4/2004 | Konishi |
| 6,828,297 | B2 | 12/2004 | Ekwuribe et al. |
| 6,858,580 | B2 | 2/2005 | Ekwuribe et al. |
| 6,867,183 | B2 | 3/2005 | Soltero et al. |
| 6,890,518 | B2 | 5/2005 | Patton et al. |
| 7,605,123 | B2 * | 10/2009 | Radhakrishnan et al. ..... 514/1.1 |
| 7,635,675 | B2 | 12/2009 | Opawale et al. |
| 7,872,095 | B2 * | 1/2011 | Radhakrishnan et al. .... 530/303 |
| 2001/0031726 | A1 | 10/2001 | Van Antwerp et al. |
| 2001/0036916 | A1 | 11/2001 | Brader |
| 2001/0041786 | A1 | 11/2001 | Brader et al. |
| 2002/0045731 | A1 | 4/2002 | Schaffer et al. |
| 2002/0082199 | A1 | 6/2002 | Brader |
| 2002/0160938 | A1 | 10/2002 | Brandenburg et al. |
| 2003/0004304 | A1 | 1/2003 | Ekwuribe et al. |
| 2003/0027995 | A1 | 2/2003 | Ekwuribe et al. |
| 2003/0050228 | A1 | 3/2003 | Ekwuribe et al. |
| 2003/0060606 | A1 | 3/2003 | Ekwuribe et al. |
| 2003/0069170 | A1 | 4/2003 | Soltero et al. |
| 2003/0083232 | A1 | 5/2003 | Soltero et al. |
| 2003/0087808 | A1 | 5/2003 | Soltero et al. |
| 2003/0144468 | A1 | 7/2003 | Ekwuribe et al. |
| 2003/0153488 | A1 | 8/2003 | May et al. |
| 2004/0077528 | A1 | 4/2004 | Steiner et al. |
| 2004/0235948 | A1 | 11/2004 | Oelze et al. |
| 2005/0025791 | A1 * | 2/2005 | Remenar et al. ............. 424/400 |
| 2005/0085498 | A1 * | 4/2005 | Byrd ............................ 514/275 |
| 2005/0113449 | A1 | 5/2005 | Renshaw |
| 2005/0222259 | A1 | 10/2005 | Bell et al. |
| 2006/0159746 | A1 | 7/2006 | Troup et al. |

FOREIGN PATENT DOCUMENTS

| | | |
|---|---|---|
| EP | 0 597 007 | 10/1996 |
| EP | 000246540 | 11/1996 |
| EP | 0 797 615 | 1/1999 |
| EP | 0 822 218 | 10/2000 |
| EP | 0835129 | 10/2003 |
| EP | 1 044 023 | 5/2005 |
| EP | 1 148 873 | 7/2005 |
| EP | 1857467 A1 | 11/2007 |
| WO | WO 95/30641 | 11/1995 |
| WO | WO 97/14740 | 4/1997 |
| WO | WO 98/07745 | 2/1998 |
| WO | WO 99/26661 | 6/1999 |
| WO | WO 00/29013 | 5/2000 |
| WO | WO 00/44361 | 8/2000 |
| WO | WO 01/12230 | 2/2001 |
| WO | WO 03/086361 | 10/2003 |
| WO | WO 2004/004779 | 1/2004 |
| WO | WO 2004/004780 | 1/2004 |
| WO | WO 2004/004781 | 1/2004 |
| WO | WO 2004/060347 | 7/2004 |
| WO | 2006/014673 A2 | 2/2006 |

OTHER PUBLICATIONS

Abraham Abuchowski et al.; Soluble Polymer-Enzyme Adducts; Enzymes as Drugs; 1981; Chapter 13, 367-383; John Wiley & Sons, New York, US.

M.J. Adams et al.; Structure of Rhombohedral 2 Zinc Insulin Crystals; Nature; 1969; pp. 491-495; vol. 224.

Vikas Agarwal et al.; Polymethyacrylate Based Microparticulates of Insulin for Oral Delivery: Preparation and in vitro Dissolution Stability in the Presence of Enzyme Inhibitors; International Journal of Pharmaceutics; (2001), 225, 31-39; Elsevier Science B.V.

Minoru Akiyama et al.; The Synthesis of new Derivatives of 1-B-D-Arabinofuranosylcytosine; Chem. Pharm. Bull.; (1978), vol. 26, No. 3 981-984; Japan. cited by other.

H. Allaudeen et al.; Orally Active Insulin: A Single Insulin Conjugate Selected for Future Studies; American Diabetes Association; Jun. 2000, Atlanta, GA, USA. cited by other.

Harry R. Allcock et al., Gel Permeation Chromatography; Contemporary Polymer Chemistry (2nd ed.) 1990 394-493, Prentice Hall, USA.

Michael Alvarsson et al.; Beneficial Effects of Insulin Versus Sulphonylurea on Insulin Secretion and Metabolic Control in Recently Diagnosed Type 2 diabetic Patients; Diabetes Care; 2003; pp. 2231-2237; vol. 26, No. 8; USA.

Steven M. Ansell et al.; Application of Oligo-(14-amino-3,6,9,12-tetraoxatetradecanoic acid) Lipid Conjugates as Steric Barrier Molecules in Liposomal Formulations; Bioconjugate Chem.; (1999), 10, 653-666; American Chemical Society.

Michiko Aoshima et al.; N4-Behenoyl-1-B-D-Arabinofuranosylcytosine as a potential New Antitumor Agent; Cancer Research; (1977), 37, 2481-2486; Japan.

David C. Baker et al.; Prodrugs of 9-B-D-Arabinofuranosyladenine. 1. Synthesis and Evaluation of Some 5'-(O-Acyl) Derivatives; Journal of Medicinal Chemistry; (1978), vol. 21, No. 12, 1218-1221; American Chemical Society.

F.G. Banting et al.; Pancreatic Extracts in the Treatment of Diabetes Mellitus; The Canadian Medical Association Journal; (1922), 141-146; The Canadian Medical Association.

M. Baudys, et al.; Stabilization and Intestinal Absorption of Human Calcitonin; Journal of Controlled Release; (1996), 39, 145-151; Elsevier Science B.V.

Miroslav Baudys et al.; Synthesis and Characterization of Different Glycosylated Derivatives of Insulin; Proceed. Intern. Symp. Control. Rel. Bioact. Mater., (1992), 19, 210-211; Controlled Release Society, Inc.

Leslie Z. Benet et al. Iontophoretic Devices for Drug Delivery; Pharmaceutical Research; (1986), vol. 3, No. 6, 318-329'; Plenum Publishing Co., USA.

G. Bentley et al.; Rhombohedral Insulin Crystal Transformation; J. Mol. Biol.; 1978; pp. 871-875; vol. 126.

Graham Bentley et al.; Structure of Insulin in 4-Zinc Insulin; Nature; 1976; vol. 261, pp. 166-168.

(56) References Cited

OTHER PUBLICATIONS

Duane T. Birnbaum et al.; Hierarchial Modeling of Phenolic Ligand Binding to 2Zn-Insulin Hexamers; Biochemistry; 1996; vol. 35; No. 17; American Chemical Society.

T.L. Blundell, et al. Protein Crystallography, (1976) pp. 323-341, Academic Press, NY USA.

E. Boccu et al.; Pharmacokinetic Properties of Polyethylene Glycol Derivatized Superoxide Dismutase; Pharmacological Research Communications; (1982), vol. 14, No. 2, 113-120.

A.J. Bone et al.; Successful Treatment of an Insulin Dependent Rat Model of Human Type 1 Diabetes with Orally Active Insulin; Department of Pharmacy, University of Brighton and Protein Delivery, Inc., Durham, North Carolina, USA.

Mark L. Brader et al.; Hybrid Insulin Cocrystals for Controlled Release Delivery; Nature Biotechnology; 2002; pp. 800-804; vol. 20; http://biotech.nature.com.

Mark L. Brader et al.; The T to R Transition in the Copper(II)-Substituted Insulin Hexamer. Anion Complexes of the R-State Species Exhibiting Type 1 and Type 2 Spectral Characteristics; Biochemistry; 1992; pp. 4691-4696; vol. 31; No. 19; American Chemical Society.

Jens Brange et al.; Chemical Stability of Insulin. 2. Formation of Higher Molecular Weight Transformation Products During Storage of Pharmaceutical Preparations; Pharmaceutical Research; (1992), vol. 9, No. 6, 727-734; Plenum Publishing Corporation.

Jens Brange et al.; Chemical Stability of Insulin. 1. Hydrolytic Degradation During Storage of Pharmaceutical Preparations; Pharmaceutical Research; (1992), vol. 9, No. 6, 715-726; Plenum Publishing Corporation.

Jens Brange et al.; Insulin Analogs with Improved Pharmacokinetic Profiles; Advanced Drug Delivery Reviews; (1999), 35, 307-335; Elsevier Science B.V.

P. Calceti et al.; Development and in vivo Evaluation of an Oral Insulin-PEG Delivery System; European Journal of Pharmaceutical Sciences; 2004; pp. 315-323; vol. 22; Elsevier B.V.

Christiane Damge et al.; Poly(alkyl cyanoacrylate) Nanospheres for Oral Administration of Insulin; Journal of Pharmaceutical Sciences; (1997), vol. 86, No. 12, 1403-1409; American Chemical Society and American Pharmaceutical Association.

Chris Dickey, Seeking Purity in the Proteomic Era, Genomics and Proteomics, May 2004, pp. 20-23.

Steven W. Dodd et al.; Reversible Adsorption of Soluble Hexameric Insulin onto the Surface of Insulin Crystals Cocrystallized iwth protamine: An Electrostatic Interaction; Pharmaceutical Research; 1995; pp. 60-68; vol. 12; No. 1; Plenum Publishing Corporation.

E.J. Dodson et al.; Structural Relationships in the Two-Zinc Insulin Hexamer; Can. J. Biochem.; 1979; vol. 57; National Research Council of Canada.

N. Ekwuribe et al.; Oral Insulin Delivery: Hydrolyzable Amphiphilic Oligomer Conjugates Prolong Glucose Reduction; Proceed. Int'l. Symp. Control. Rel. Bioact. Mater.; (1999), 26, 147-148; Controlled Release Society, Inc.

Abstract of Nnochiri Ekwuribe; Conjugation-Stabilized Polypeptide Compositions, Therapeutic Delivery and Diagnostic Formulations Compriisng Same, and Method of Making and Using the Same; Biotechnology Advances; (1996), vol. 14, Issue 4, 575-576; Elsevier Science Direct, USA.

Wolfgang H. Fischer et al.; A Shortened Insulin with Full in vitro Potency; Biol. Chem. Hoppe-Seyler; 1985; pp. 521-525; vol. 366; Walter de Gruyter & Co., New York.

T. Forst et al.; New Aspects on Biological Activity of C-peptide in IDDM Patients; Experimental and Clinical Endocrinology Diabetes; (1998), 106, 270-276; Johann Ambrosius Barth.

Wayne Genck; Crystal Clear—An Extremely Selective Process, Crystallization can be a Powerful Separation Tool. But, to Optimize product, you must clearly understand.; Filtration/Separation; 2003; pp. 63-67; www.chemicalprocessing.com.

Jose Goldman et al.; Zinc Binding, Circular Dichroism, and Equilibrium Sedimentation Studies on Insulin (Bovine) and Several of Its Derivatives; Biochemistry; 1974; pp. 4566-4574; vol. 13, No. 22; American Chemical Society.

P.T. Grant et al.; Differences in the Nature of the Interaction of Insulin and Proinsulin with Zinc; Biochemistry; 1972; pp. 433-440; vol. 126; Great Britain.

Angel Guzman et al; Effects of Fatty Ethers and Stearic Acid on the Gastrointestinal Absorption of Insulin; PRHSJ; (1990), vol. 9, No. 2, 155-159; San Juan, PR.

J. Milton Harris; Laboratory Synthesis of Polyethylene Glycol Derivatives; JMS-Rev. Macromol. Chem. Phys.; (1985), C25(3), 325-373; Marcel Dekker, Inc.

Kenneth D. Hinds et al.; Effects of PEG Conjugation on Insulin Properties; Advanced Drug Delivery Reviews; 2002; pp. 505-530; vol. 54; Elsevier Science B.V.

Edgar Jacoby et al.; Structure and Dynamics of a Protein Assembly; J. Mol. Biol.; 1996; pp. 136-157; vol. 258; Academic Press Limited.

Kenneth James et al., Effects of Amphiphilic Oligomers on Oral Insulin Conjugates, Part 3, Solubility and Protease Stability, American Chemical Society, Mar. 2003 USA.

Anna Jen et al.; Diamonds in the Rough: Protein Crystals from a Formulation Perspective; Pharmaceutical Research; 2001; pp. 1483-1488; vol. 18, No. 11; Plenum Publishing Corporation.

B. Radha Krishnan et al.; Chemical Modification of Insulin with Amphiphilic Polymers Improves Intestinal Delivery; Proceed. Int'l. Symp. Control. Rel. Bioact. Mater.; (1998), 25, 124-125; Controlled Release Society, Inc.

Jong-Hoon Lee et al.; Polymeric nanoparticle composed of fatty acids and poly(ethylene glycol) as a drug carrier; International Journal of Pharmaceutics; 2003; 251, pp. 23-32; Elsevier Science B.V.

Yuping Li et al.; Dissociation of Insulin Oligomers by Bile Salt Micelles and Its Effect on a-Chymotrypsin-Mediated Proteolytic Degradation; Pharmaceutical Research; 1992; pp. 864-869; vol. 9; No. 7; Plenum Publishing Corporation.

Kang Choon Lee et al.; Isolation, Characterization, and Stability of Positional Isomers of Mono-PEGylated Salmon Calcitonins; Pharmaceutical Research; 1999; vol. 16, No. 6, pp. 813-818; Plenum Publishing Corporation.

Haeshin Lee et al.; Preparation and Characterization of Mono-PEGylated Epidermal Growth Factor: Evaluation of in Vitro Biologic Activity; Pharmaceutical Research; 2002; vol. 19, No. 6, pp. 845-851; Plenum Publishing Corporation.

D.G. Lindsay et al.; The Acetylation of Insulin; Biochem. J.; (1971), 121, 737-745; Great Britain.

Andrea Lucke et al.; Biodegradable poly(D,L-lactic acid)-poly(ethylene glycol)-monomethyl ether diblock copolymers: structures and surface properties relevant to their use as biomaterials; Biomaterials; 2000; 21, pp. 2361-2370; Elsevier Science Ltd.

Navdeep B. Malkar et al.; Characterization of Peptide—Amphiphiles Possessing Cellular Activation Sequences; Biomacromolecules; 2003; Published on the web by the American Chemical Society.

Navdeep Malkar et al. Effects of Amphiphilic Oligomers on Oral Insulin Conjugates, Part 2, Conformation Changes of Conjugates, ACS Mar. 2003 USA.

Navdeep B. Malkar et al.; Conjugation of Peptide Therapeutics Using Small, Mono-Dispersed Amphiphilic Oligomers for Oral Delivery; AAPS-Biotech Conference; 2005; USA.

A.N. McLeod et al.; High-Performance Liquid Chromatography of Insulin Accessibility and Flexibility; Chrom. 22 076; 1990; Elsevier Science Publishers B.V.

Mark Miller, Effects of Amphiphilic Oligomers on Oral Insulin Conjugates, Part 1, Synthesis and Activity; ACS 2003 USA.

Nektar Advanced PEGylation—Polyethylene Glycol and Derivatives for Advanced PEGylation; Catalog 2004, pp. 1-24; USA.

H. Paul Neubauer et al.; Influence of Polyethylene Glycol Insulin on lipid Tissues of Experimental Animals; Diabetes; (1983), vol. 32, 953-958; Germany.

David C. Pang; Bridging Gaps in Drug Discovery and Development; Pharmaceutical Technology; (1998), 22, 11, 82-94; USA.

Giovanni M. Pauletti et al.; Improvement of Oral Peptide Bioavailability: Peptidomimetics and Prodrug Strategies; Advanced Drug Delivery Reviews; (1997), 27, 235-256; Elsevier Science B.V.

(56) References Cited

OTHER PUBLICATIONS

Allen H. Pekar et al.; Conformation of Proinsulin. A Comparison of Insulin and Proinsulin Self-Association at Neutral pH; Biochemistry; 1972; pp. 4013-4016; vol. 11; No. 22; American Chemical Society.

Michael J. Pikal et al.; The Stability of Insulin in Crystalline and amorphous Solids: Observation of Greater Stability for the Amorphous Form; Pharmaceutical Research; 1997; pp. 1379-1387; vol. 19; No. 10; Plenum Publishing Corporation.

Y. Pocker et al.; Conformational Dynamics of Insulin in Solution. Circular Dichroic Studies; Biochemistry; 1980; pp. 5043-5049; vol. 19, No. 22; American Chemical Society.

Abstract of Monica E. Puskas et al.; Investigation of Chymotrypsin Digestion Profile of Orally Active Insulin Conjugate Him2; AAPSPharmSci; (2001), vol. 3, No. 3, Arlington, VA, USA.

Quanta Biodesign Labeling, Derivatization and Crosslinking Reagents for Biological and Related Materials with dPEG; Quanta Biodesign; 2003; p. 13; USA.

Matthew C. Riddle; Making the Transition from Oral to Insulin Therapy; The American Journal of Medicine; 2005; pp. 14S-20S; vol. 118, No. 5A; Elsevier Inc.

J. Schlichtkrull; Insulin Crystals; Acta Chemica Scandinavica; 1956; pp. 1455-1459; vol. 10, No. 9.

Steven E. Shoelson et al.; Mutations at the Dimer, Hexamer, and Receptor-Binding Surfaces of Insulin Independently Affect Insulin-Insulin and Insulin-Receptor Interactions; Biochemistry; 1992; pp. 1757-1767; vol. 31; No. 6; American Chemical Society.

Soon H. Song et al.; Direct Measurement of Pulsatile Insulin Secretion from the Portal Vein in Human Subjects; The Journal of Clinical Endocrinology and Metabolism; (2000), vol. 85, No. 12, 4491-4499; The Endocrine Society, USA.

J. Gordon Still et al.; Effects of Orally Active Modified Insulin in Type 1 Diabetic Patients; 2001 Annual Meeting of the American Society for Clinical Pharmacology and Therapeutics; Orlando, Florida, USA.

J. Gordon Still et al.; Oral Insulin Development; Presentation made in London, England; (2000); Protein Delivery Incorporated, RTP, North Carolina, USA.

J.G. Still et al.; Magnitude and Variability of Pharmacokinetic and Glucodynamic Responses to Modified Human Insulin Administered Orally to Healthy Volunteers; Diabetes Research and Clinical Practice; (2002), vol. 56, Supp. 1, S77; USA.

Reto Stocklin et al.; A Stable Isotope Dilution Assay for the in vivo Determination of Insulin Levels in Humans by Mass Spectrometry; Diabetes; (1997), vol. 46, No. 1, p. 44(7), 1-8; American Diabetes Association.

Takashi Uchio et al.; Site-Specific Insulin Conjugates with Enhanced Stability and Extended Action Profile; Advanced Drug Delivery Reviews; (1999), 35, 289-306; Elsevier Science B.V.

Michael A. Weiss et al.; Heteronuclear 2D NMR Studies of an Engineered Insulin Monomer: Assignment and Characterization of the Receptor-Binding Surface by Selective . . . ; Biochemistry; 1991; pp. 7373-7389; vol. 30; No. 30; American Chemical Society.

Michael A. Weiss et al.; Two-Dimensional NMR and Photo-CIDNP Studies of the Insulin Monomer: Assignment of Aromatic Resonances with Application to Protein Folding, Structure, and Dynamics; Biochemistry; 1989; pp. 9855-9873; vol. 28; No. 23; American Chemical Society.

Jean L. Whittingham et al.; Crystal Structure of a Prolonged-Acting Insulin with Albumin-Binding Properties; Biochemistry; 1997; pp. 2826-2831; vol. 36; No. 10; American Chemical Society.

S. J. Wodak et al.; Simulation of Conformational Changes in 2 Zn Insulin; J. Mol. Biol.; 1984; pp. 317-322; vol. 181.

A. Wollmer et al.; Correlation of Structural Details of Insulin in the Crystal and in Solution; Insulin, Chemistry, Structure and Function of Insulin and Related Hormones; 1980; pp. 27-31; Walter de Gruyter & Co., New York.

Ling Xie et al.; Comparison of Secondary Structures of Insulin and Proinsulin by FTIR; Journal of Protein Chemistry; 1993; pp. 483-487; vol. 12, No. 4; Plenum Publishing Corporation.

S. Zalipsky et al., Attachment of Drugs to Polyethylene Glycols; Eur. Polym. Journal; (1983), vol. 19, No. 12, 1177-1183; Great Britain.

S. Zalipsky et al., Peptide Attachment to Extremities of Liposomal Surface Grafted PEF Chains: Preparation of Long-Circulating Form of Laminin Pentapeptide, YIGSR; Bioconjugate Chem. (1995), 6, 705-708; American Chemical Society.

The Pharmacopoeia of Japan (General Notices etc.) Thirteenth editions, First issue, "tablet", Hirokawa-Shoten Ltd., Jul. 10, 1996, A-97 to A-104.

Japanese Pharmaceutical Excipients Directory 2007, First edition, International Pharmaceutical Excipients Council Japan, Yakuji Nippo Limited, Jul. 25, 2007, pp. 66 and 93.

Japanese Office Action , issued by the Japanese Patent Office, corresponding to Japanese Patent Application No. 2010-529507, issued on Jun. 9, 2015.

\* cited by examiner

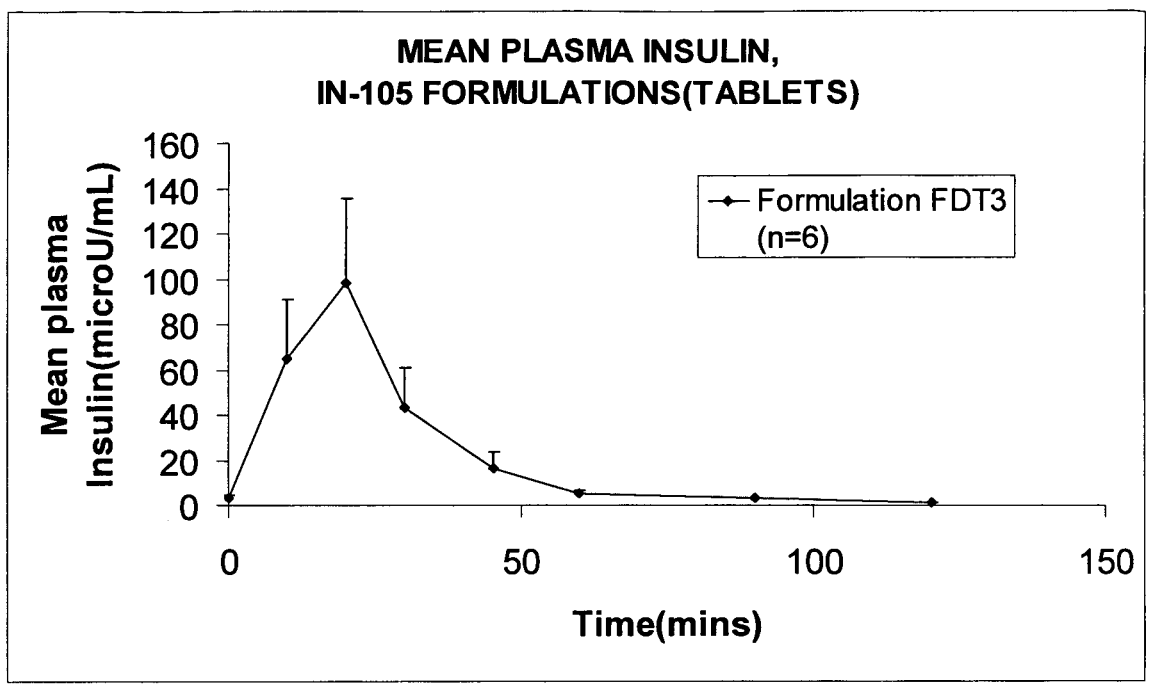
FIG 1: Mean plasma insulin profile – IN-105 formulation tablets (FDT-3)

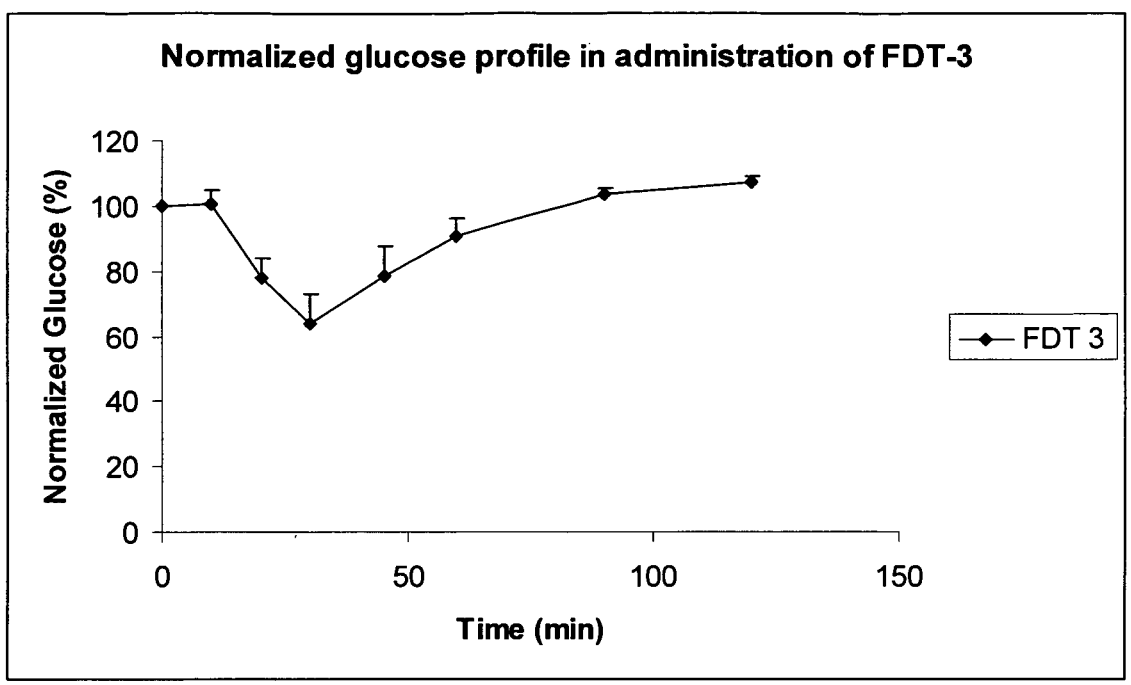
FIG 2: Normalised glucose profile in administration of FDT-3

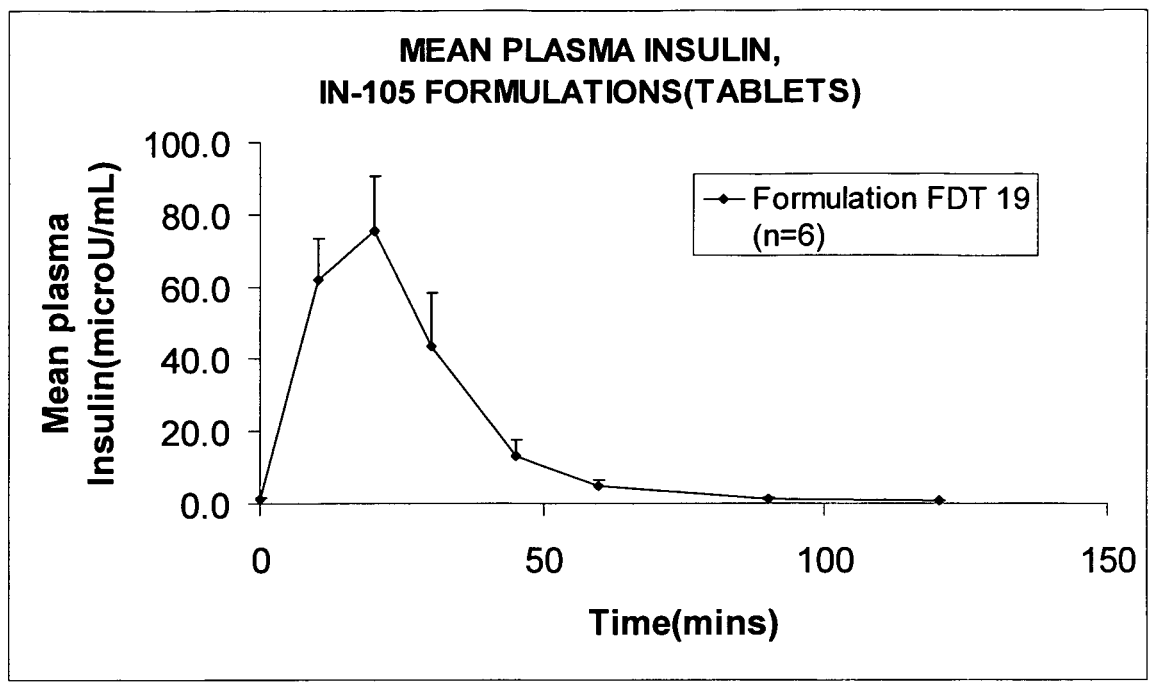
FIG 3: Mean plasma insulin profile – IN-105 formulation tablets (FDT-19)

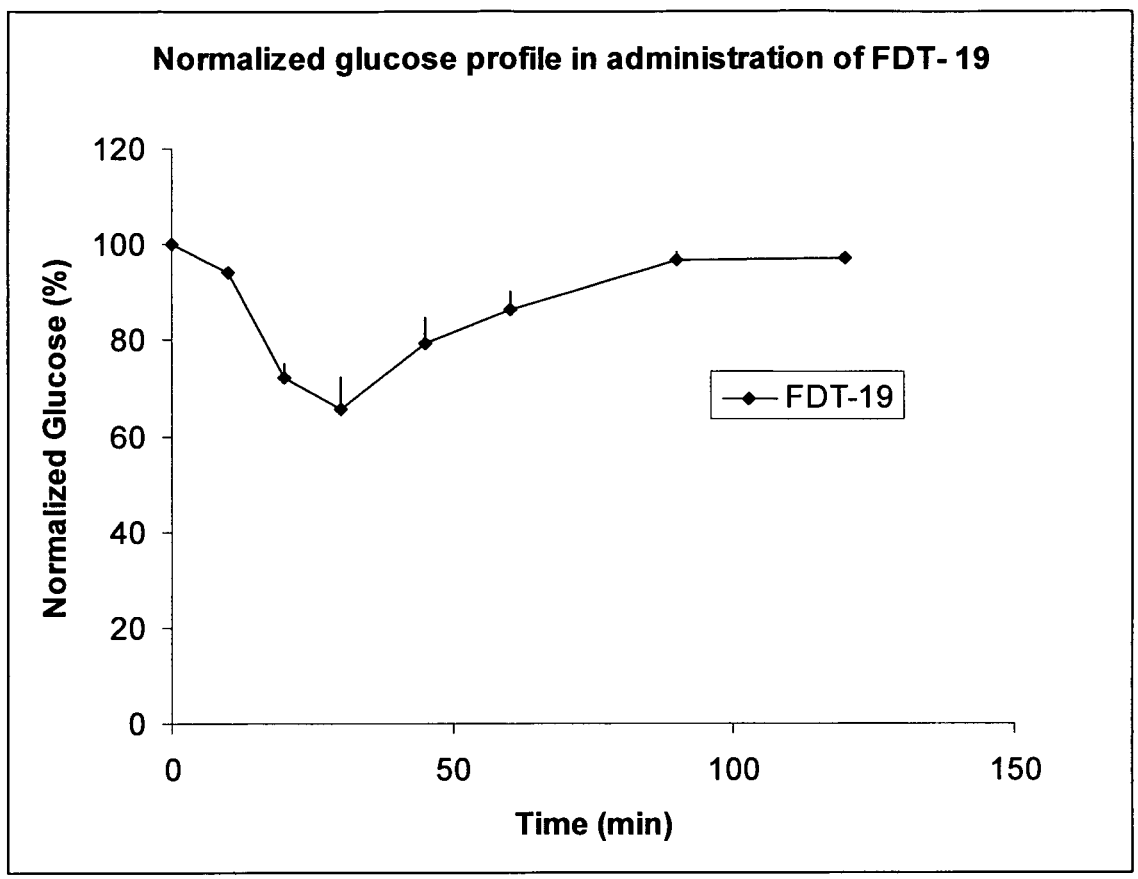
FIG 4: Normalised glucose profile in administration of FDT-19

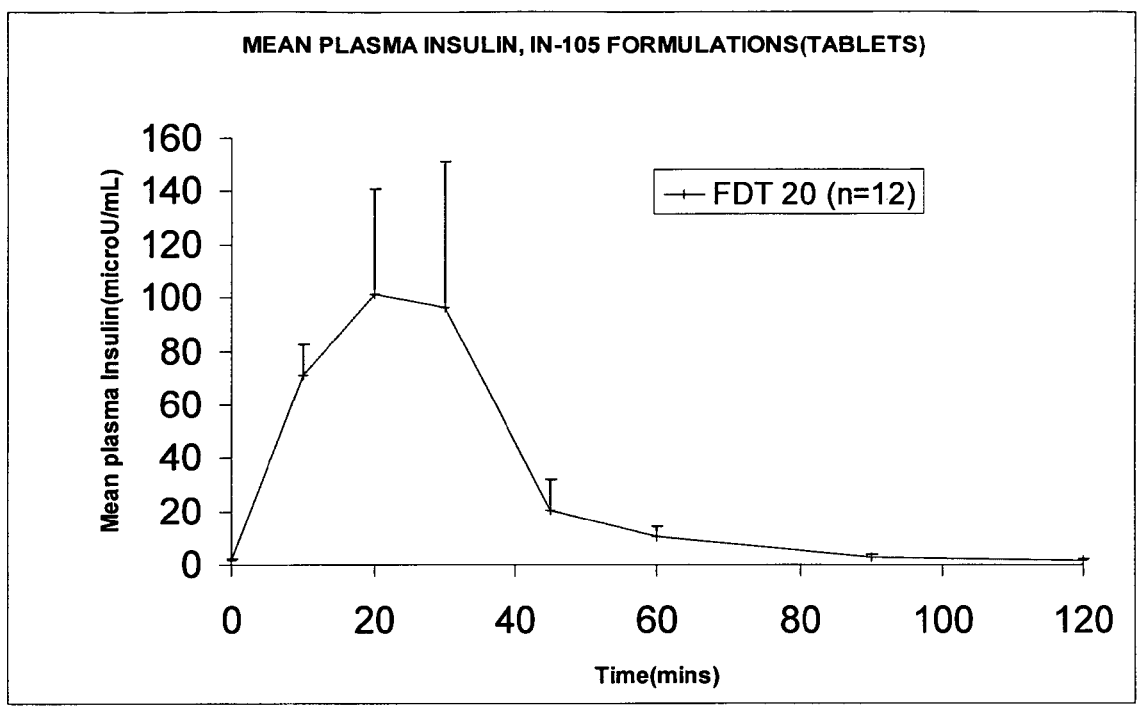
FIG 5: Mean plasma insulin profile – IN-105 formulation tablets (FDT-20)

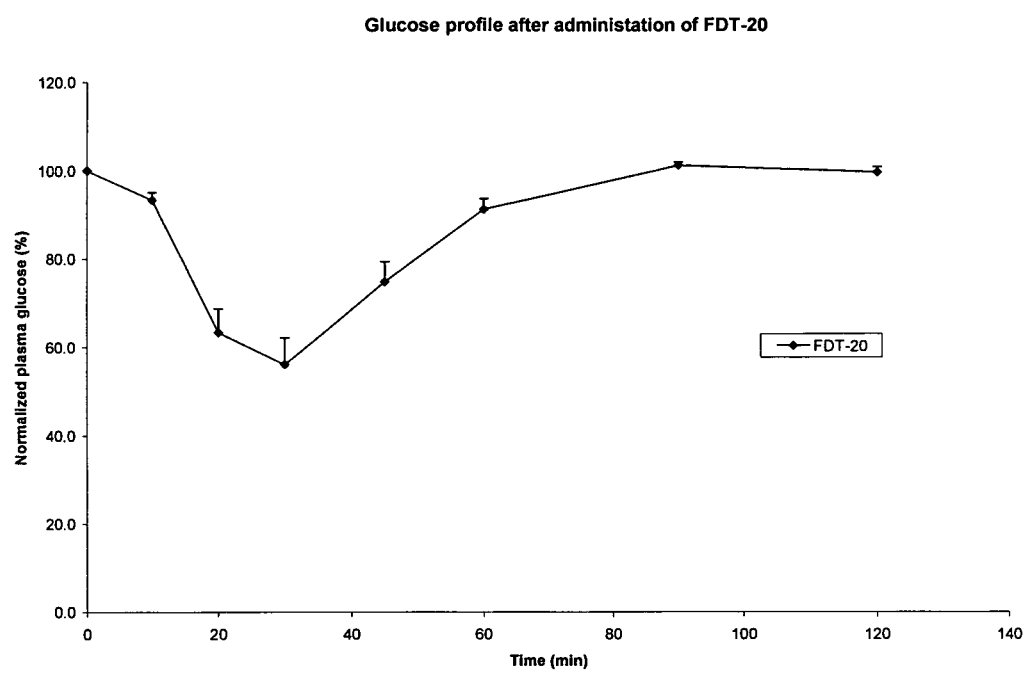
FIG 6: Glucose profile after administration of FDT-20

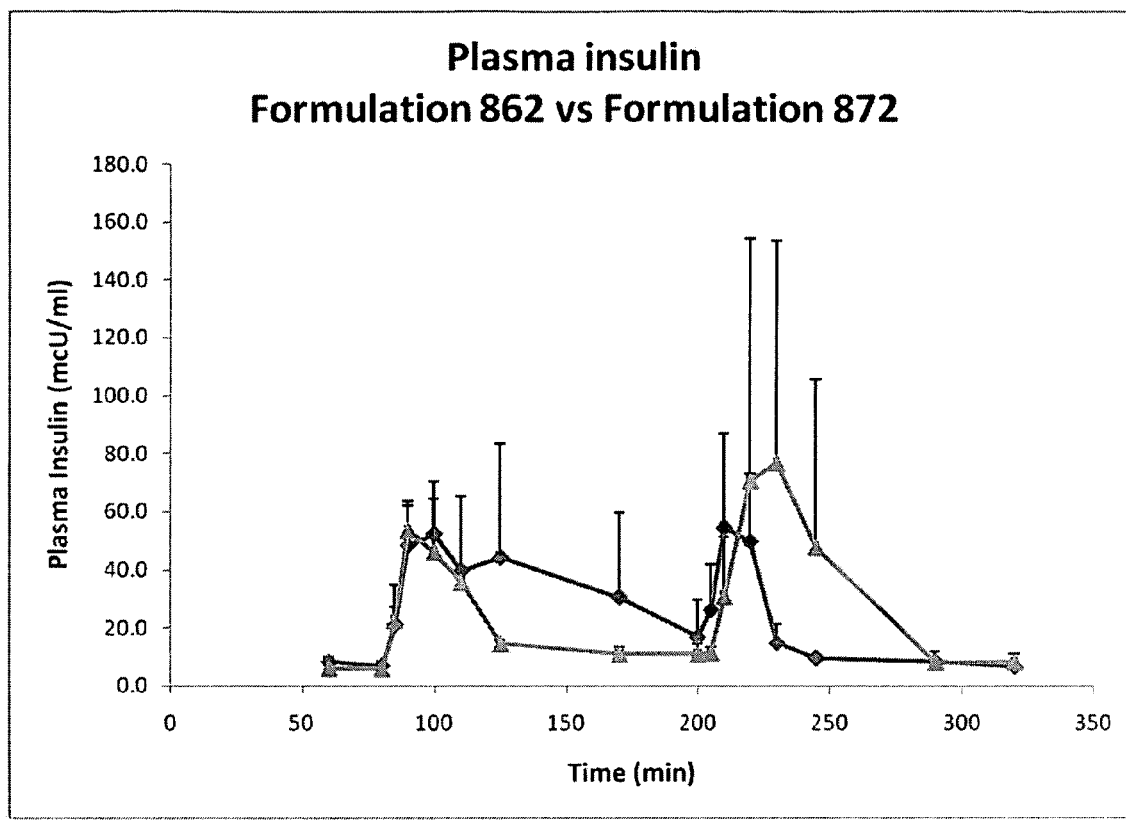
FIG 7. Plasma Insulin Profile

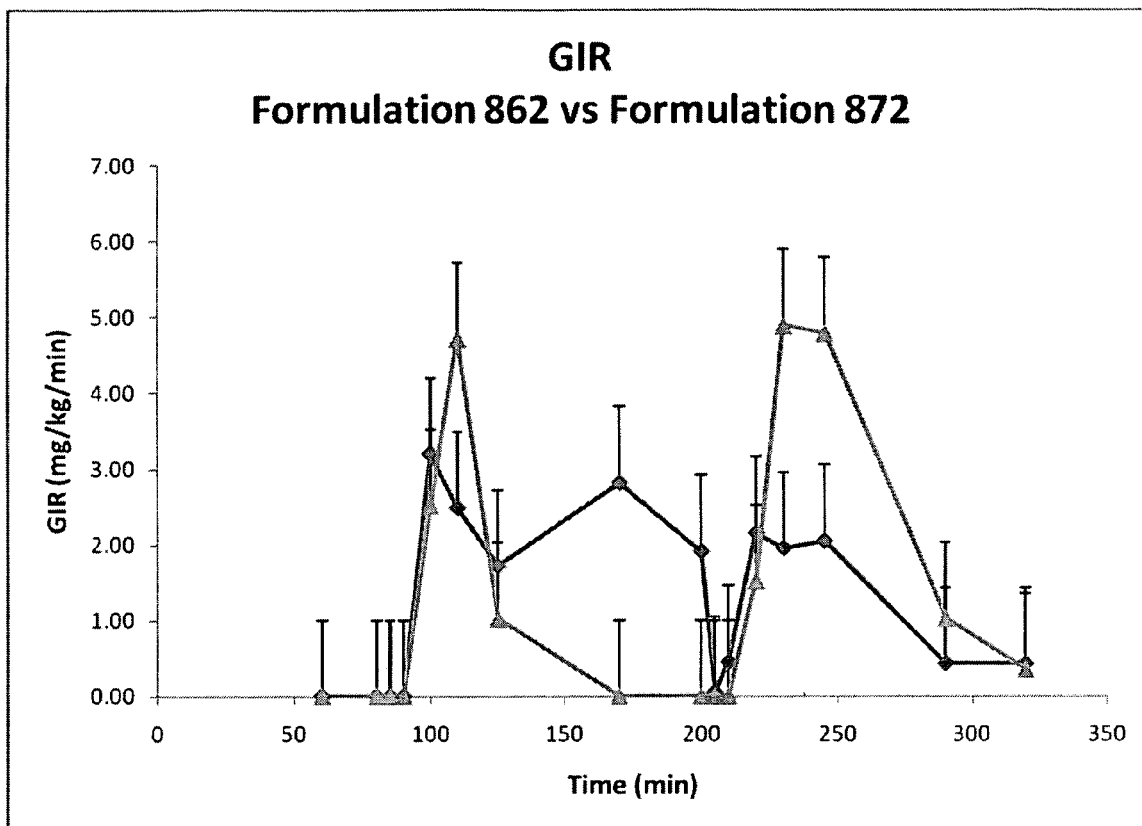
FIG 8. Glucose Infusion Rate Profile

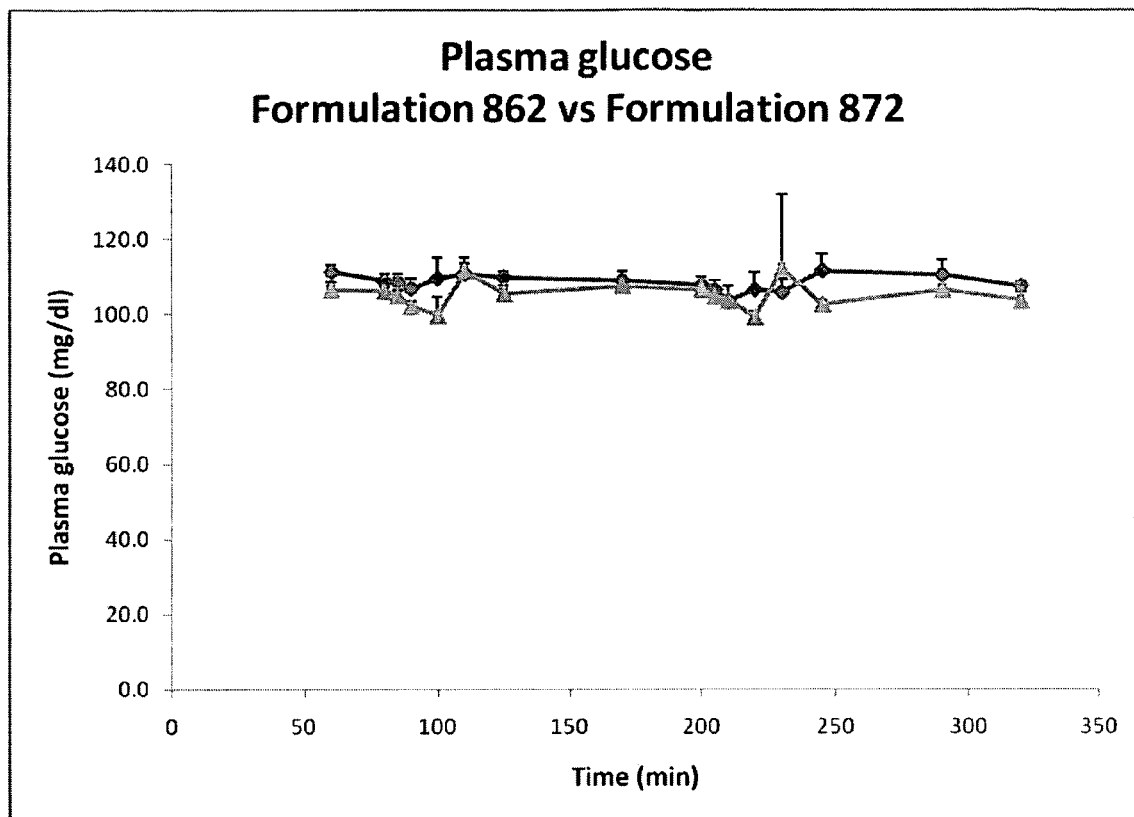
FIG 9. Plasma Glucose Profile

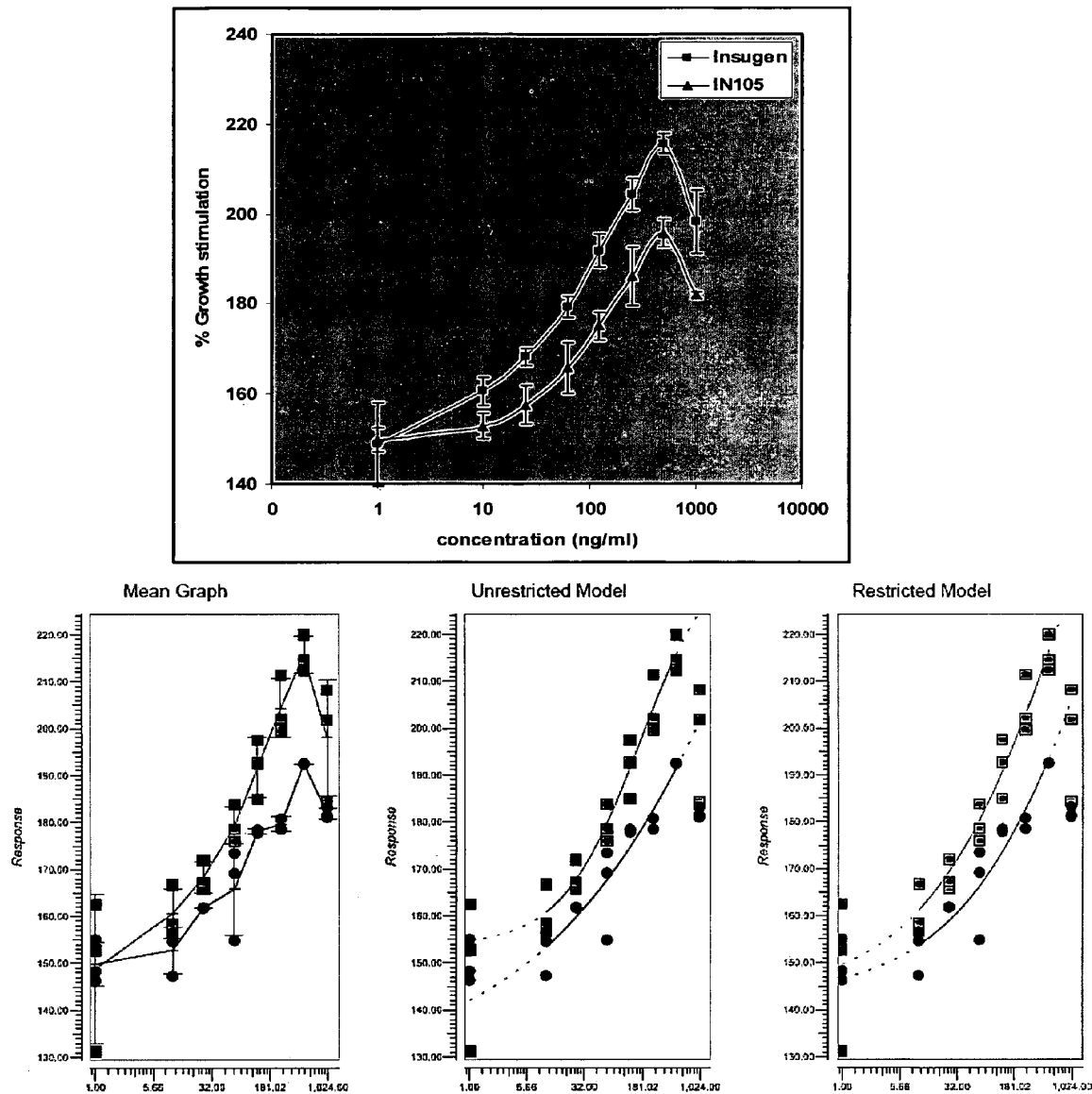
FIG 10: Parellelism and linearity of the bioassay across various concentrations of Insugen ® and In-105 determined by the PLA software. The data represents average ± SEM of triplicate values of an experiment.

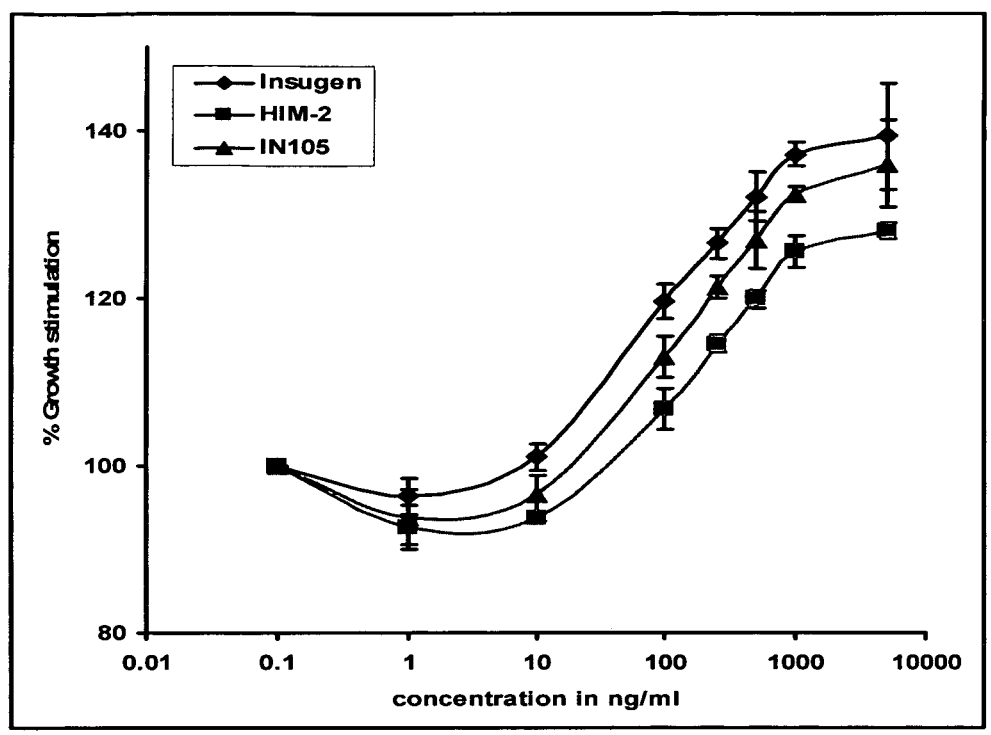
FIG 11: Mitogenic potency compared of Insugen versus IN-105 and HIM-2 from PLA analysis using 4 points in a linear range.

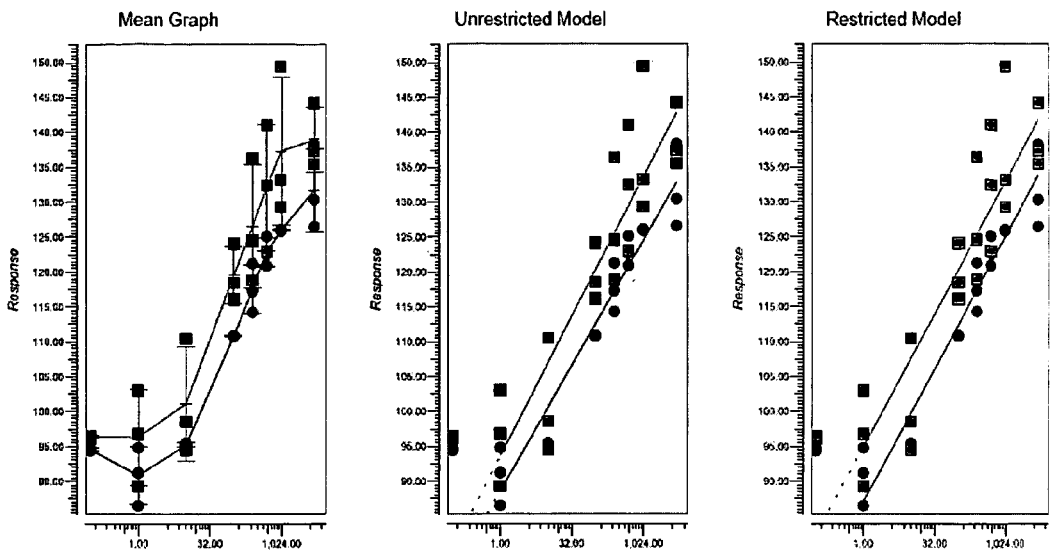
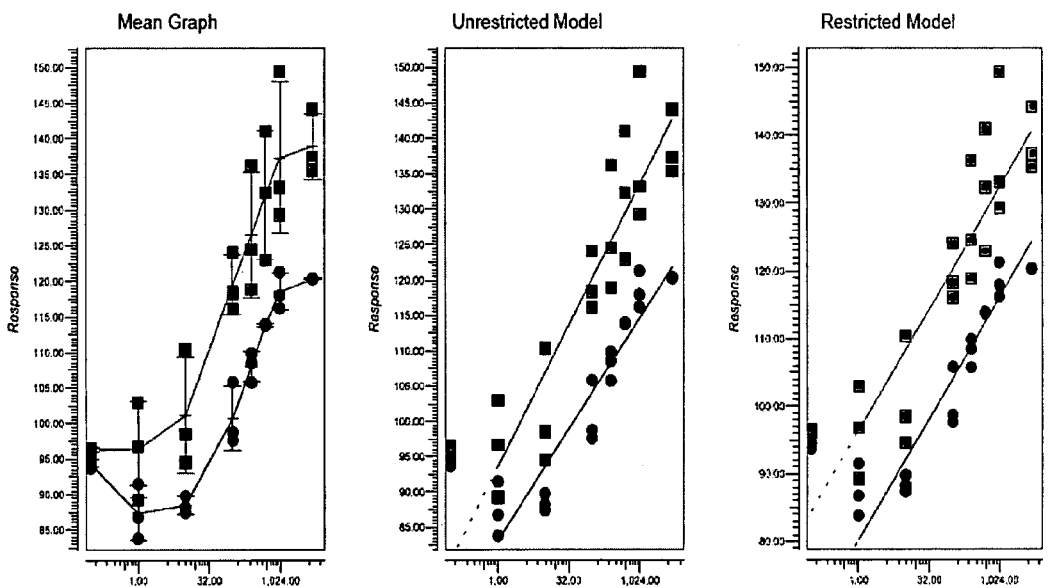
FIG 12 : Parallelism and linearity of the bioassay across various concentrations of Insugen (R) versus IN105 (A) and Insugen versus HIM-2 (B) determined by the PLA software. The data represents average ± SEM of triplicate values of an experiment.

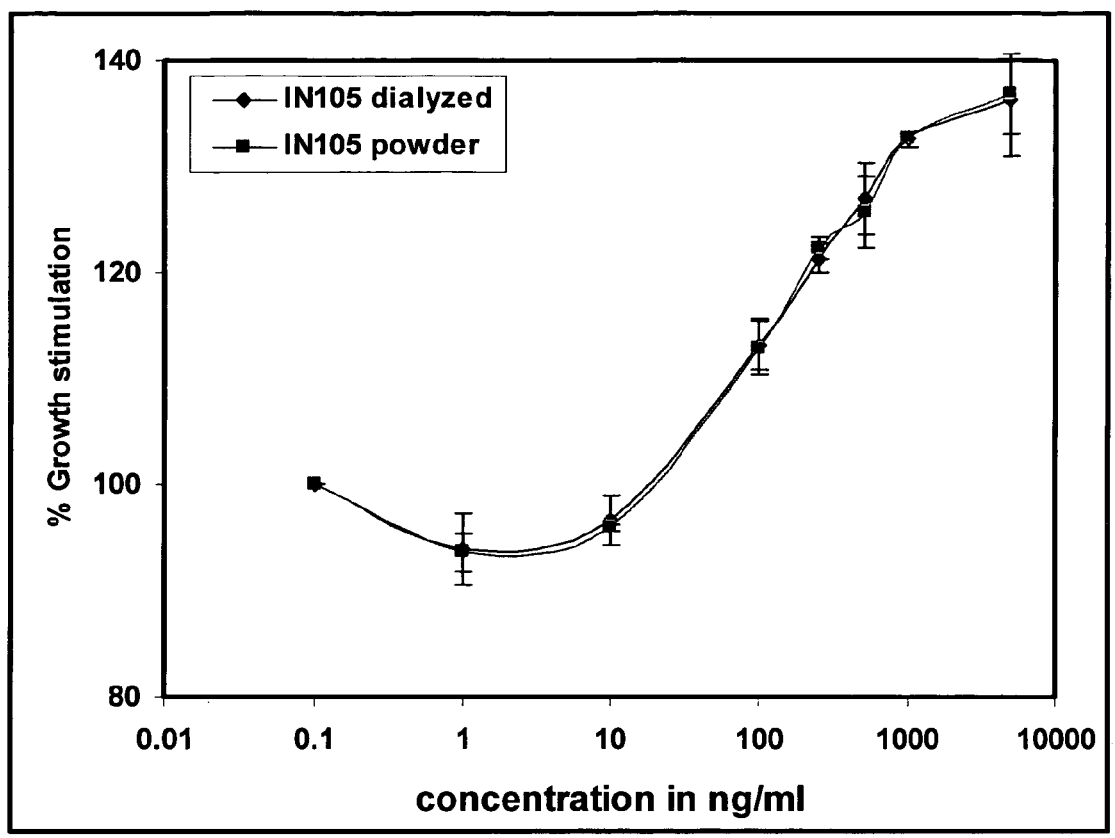
FIG 13: Mitogenic activity of IN-105 dialyzed compared with IN-105 powder for PLA analysis using a 4 points in a linear range.

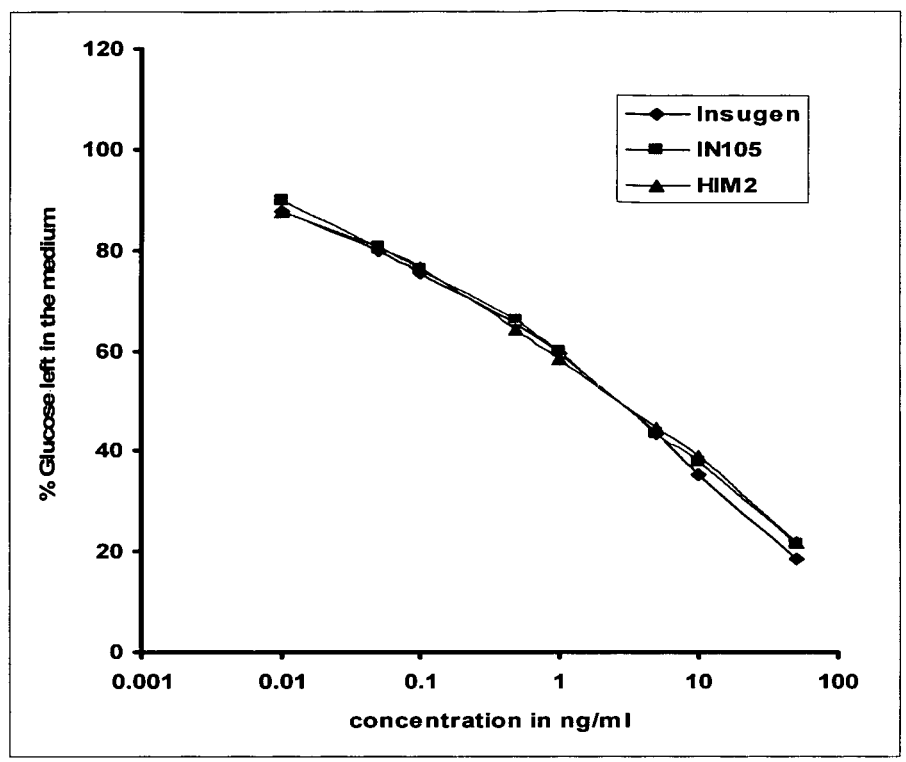
FIG 14: Comparison of Metabolic Potency between Insugen (R), IN105 and HIM-2.

A)
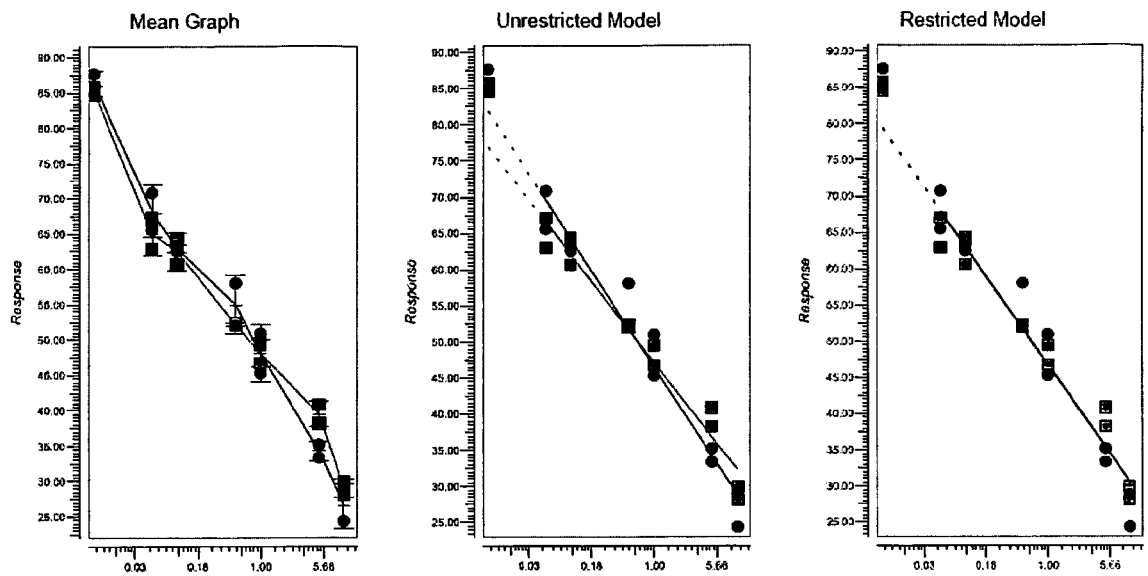
B
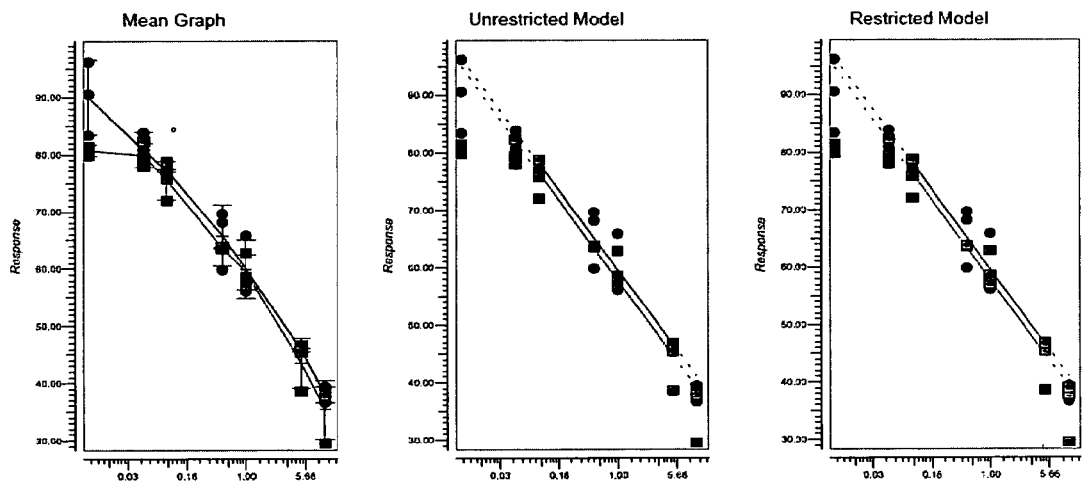
FIG 15: Parallelism and linearity of the bioassay across various concentrations of Insugen (R) versus IN105 (A) and Insugen versus HIM-2 (B) determined by the PLA software. The data represents average ± SEM of triplicate values of an experiment.

A)
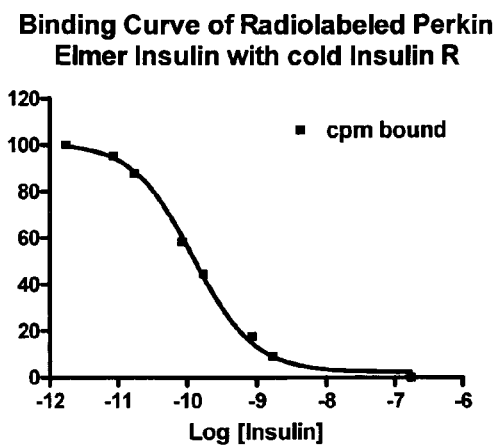
B)
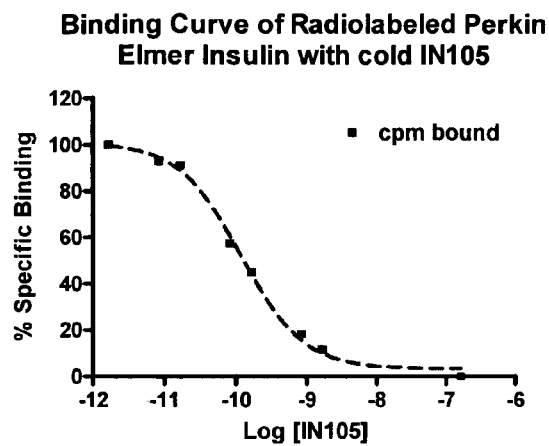
C)
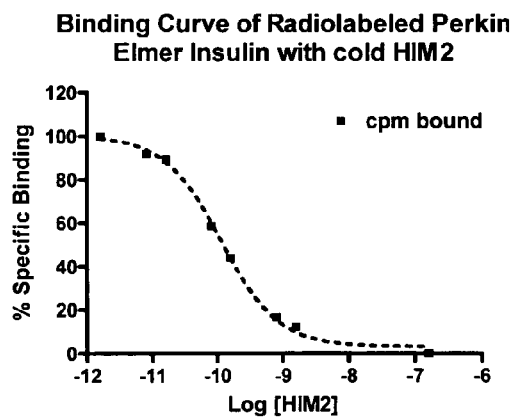
FIG 16: One Site Competition Curves of (A) Insugen (R), (B) IN105 and (C) HIM-2, respectively. The curves were determined by the Graph Pad version-4 software. The data represents average of triplicate values of an experiment.

ORALLY ADMINISTRABLE SOLID PHARMACEUTICAL COMPOSITION AND A PROCESS THEREOF

FIELD OF THE INVENTION

The invention relates to improvised pharmaceutical compositions permitting ingestion via oral delivery of proteins/peptides or their conjugates, and/or cation-insulin conjugate complexes demonstrating desirable pharmacokinetic profiles and potency in efficacy models of diabetes in dogs and humans. A preferred formulation comprises 0.01%-20% w/w of insulin, insulin compound conjugates, and/or cation insulin conjugates, 10%-60% w/w of one or more fatty acid components selected from saturated or unsaturated C4-C12 fatty acids and/or salts of such fatty acids and additionally contains optimal amounts of other pharmaceutically suitable polymer excipients which permit improved solubility, dissolution rate and effective bioavailability of poorly water soluble compositions and consistent in-vivo release profiles upon scalability during manufacture. A further aspect of the invention features the process of preparing the aforesaid formulations.

BACKGROUND OF THE INVENTION

Conventional subcutaneous routes of insulin administration are increasingly being researched to be replaced by oral drug delivery mechanisms that would not alter their physiological clinical activity. Problems confronted in this field of art in designing an effective oral drug delivery system for biological macromolecules has been mainly attributed to its susceptibility to enzymatic degradation and low epithelial permeability. Further, the structure and conformation of insulin are easily altered when exposed to formulation and process conditions leading to a loss of biological activity. Some of the approaches to combat these limitations involved the use of insulin analogs, administration of peptides such as amylin, glucagon-like peptide, C-peptides, inhaled forms, intranasal forms which have not satisfactorily addressed the limitations of bioavailability individually.

There is a need in the art for pharmaceutically acceptable complexes including derivatized insulin conjugates having increased bioavailability or other improved pharmaceutical attributes relative to the existing conjugates. Furthermore these improved conjugates need to be delivered in the form of a stable and improvised formulation that easily maximizes the benefits of oral delivery of proteins. The instant invention applies a combined approach of an improved insulin conjugate with increased bioavailability and an improved formulation to address the limitations of insulin delivery.

Examples of insulin compounds include human insulin, lyspro insulin, des30 insulin, native proinsulin, artificial proinsulins, etc. The cation component may, for example, be a divalent metal cation selected from the group consisting of $Zn^{++}$, $Mn^{++}$, $Ca^{++}$, $Fe^{++}$, $Ni^{++}$, $Cu^{++}$, $Co^{++}$ and $Mg^{++}$. The cation-insulin compound conjugate complexes also include a modifying moiety coupled (e g., covalently or ionically) to the insulin compound to provide an insulin compound conjugate. Further, the modifying moiety is selected to render the insulin compound conjugate equally or more soluble than a corresponding unconjugated insulin compound, and the water solubility of the insulin compound conjugate is decreased by the addition of zinc. The modifying moiety is selected to render the insulin compound conjugate equally or more soluble than a corresponding unconjugated insulin compound; the water solubility of the insulin compound conjugate is decreased by the addition of zinc; and water solubility of the complex is greater than the water solubility of insulin compound.

Examples of suitable modifying moieties and insulin conjugates useful in the preparation of compositions can be found in U.S. Pat. Nos. 7,060,675, 6,303,569, 6,214,330, 6,113,906, 5,985,263, 5,900,402, 5,681,811, 5,637,749, 5,612,640, 5,567,422, 5,405,877, 5,359,030 the entire disclosures of which are incorporated herein by reference. Additional examples of such cation-insulin compound conjugate complexes are provided in US patent applications US2003/083232, US 2006/0019873 and US2006/0019874.

In contrary to the existing prior art, the compounds of the present invention exhibit reduced mitogenic potential which is almost three fold lower than that of Insugen®.

Insulin binds and activates its cognate, the insulin receptor (IR) with sub-nanomolar affinity. Insulin also binds the structurally related Insulin growth factor receptor (IGFR) but with 1000 fold lower affinity than the insulin receptor. At physiological insulin concentrations the IGFR therefore does not play any role in mediating the effects of insulin. However at very high insulin concentrations (diabetic patients receiving insulin) it exerts mitogenic affects via the IGFR which transmits growth stimuli more efficiently than the insulin receptor (Lammers R, et al., EMBO 1989).

One of the earlier identified insulin analogs with modification at the aspartic acid B10 residue was aimed at providing a fast acting insulin effect, however the modification in turn led to a significant increase in the mitogenicity of that analog [Drejer, K., The bioactivity of insulin analogues from in vitro receptor binding to in vivo glucose uptake. Diabetes Metab Rev, 1992. 8(3): p. 259-85]. A study was performed to study binding of several insulin analogs to the insulin growth factor-1 (IGF-1) receptor and the insulin receptor. The binding constants were measured and correlated to the metabolic and mitogenic potency of the insulin analogs studied [Kurtzhals, P., et al., Correlations of receptor binding and metabolic and mitogenic potencies of insulin analogs designed for clinical use. Diabetes, 2000. 49(6): p. 999-1005.] As per the studies conducted, compared to regular insulin, insulin lispro, insulin aspart, and insulin glargine had minimal change in binding to the insulin receptor, whereas insulin detemir was significantly lower. Each of these analogs had similar or increased dissociation rates from the IGF receptor, which was correlated to their mitogenic behavior.

The mitogenic potency of proteins/peptides and their conjugates, cation-peptide conjugate complexes, cation-insulin conjugate complexes are of prime concern attributed to the risk of increased mitogenicity and growth of human mammary epithelial cells. Studies have proven that the binding of IGF-1 of insulin aspart was similar to that of native human insulin. Insulin lispro and insulin glargine had 1.5 to 6.5 fold increase in binding affinity to the IGF-1 receptor, respectively implying that insulin glargine has a significantly greater mitogenic response.

The long term effects of the mitogenic properties of insulin analogs, their conjugates, cation-peptide conjugate complexes, cation-insulin conjugate complexes continues to be an important factor to be considered. The Points to consider document CPMP/SWP/372/01 on the non-clinical assessment of the carcinogenic potential of insulin analogues states: "Native human insulin has, in addition to its metabolic actions, a weak mitogenic effect. This effect has become important for the safety of insulin analogues, since structural modifications of the insulin molecule could increase the mitogenic potency, possibly resulting in growth stimulation of pre-existing neoplasms." "Although enhanced insulin-like growth factor 1 (IGF-1) receptor activation and/or aberrant signalling through the insulin receptor have been implicated, the mechanism(s) responsible for the mitogenic activity of insulin analogues remain to be clarified."

As an evidence that IGF-1 promotes colonic-, breast-, prostatic-, and lung cancer growth is accumulating, there exists a need for the development of proteins/peptides and their conjugates, cation-peptide conjugate complexes, cation-insulin conjugate complexes with minimal mitogenic risk which is assessed in a cell proliferation assay and that may be termed safe for long term therapy.

Current invention relates to protein/peptides, their conjugates, and/or cation-polypeptide conjugate complexes displaying three folds lower mitogenic properties in comparison to Insugen). Further aspects of the present invention are directed to the fact that excipients in the drug product does not statistically impact the mitogenic potency characteristics of the drug substance.

Another aspect of the invention relates to improvised pharmaceutical compositions permitting ingestion via oral delivery of proteins/peptides or their conjugates, and/or cation-insulin conjugate complexes demonstrating desirable pharmacokinetic profiles and potency in efficacy models of diabetes in dogs and humans.

WO00/50012 discloses solid oral dosage forms comprising a drug and an enhancer, wherein the enhancer is a salt of a medium chain fatty acid with a carbon chain length of about 6-20 carbon atoms. US2006/0018874 cover a solid pharmaceutical composition formulated for oral administration by ingestion, having 0.1 to 75% w/w fatty acid component, where the fatty acid component comprises saturated or unsaturated fatty acids and/or salts and a therapeutic agent.

Notwithstanding the foregoing, there still exists a need for manufacture of viable oral insulin formulations that can overcome problems associated with loss of biological activity during manufacture and at the same time exhibit enhanced resistance to enzymatic degradation in-vivo post ingestion. The present invention addresses both requirements. Thereby, the invention addresses the problems confronted in the art to design a highly effective oral insulin-conjugate drug delivery mechanism.

The invention exhibits various advantages with respect to the dosing and convenient method of administration. The invention constitutes yet another advantage over the prior art compositions as the inventors propose that the claimed rationally designed oral formulation of IN-105 with measured components of other excipients and the process of manufacturing the orally administrable tablets are easily scalable. Further, attributed to this rationally designed oral formulation and the process of making the same, the scalability factor does not impact the in-vivo drug performance or its in-vivo release profile.

Currently available oral insulin formulations exhibit low levels of stability precluding possibilities of oral administration of such therapeutics. One of the most significant aspect of the present invention is characterized in the fact that the instant oral insulin formulation is stable over a range of temperature without adversely impacting various parameters of the tablet stability such as hardness, disintegration time, accumulation of high molecular weight impurities and dissolution rate. The tablets thus made show excellent stability even under accelerated stability conditions of 40° C./75% relative humidity. The inherent stable characteristics of the molecule and the manufacturing methods attribute to the stable nature of the formulation.

Another aspect of the invention relates to improved pharmaceutical compositions of cation-insulin conjugate complexes prepared by a scalable spray drying procedure said process comprising steps of preparing an aqueous suspension of the cation-insulin conjugate complex and at least one fatty acid component with optionally one or more pharmaceutically acceptable excipients.

In a typical process for fine particles using a spray drying process, material, such as the ingredient which is intended to form the bulk of the particle is dissolved in an appropriate solvent to form a solution. Alternatively, the material intended to be spray dried can be suspended or emulsified in a non-solvent to form a suspension or emulsion. Other components, such as drugs, pharmaceutically acceptable excipients or pore forming agents optionally are added at this stage. The solution then is atomized to form a fine mist of droplets. The droplets immediately enter a drying chamber where they contact a drying gas. The solvent is evaporated from the droplets into the drying gas to solidify the droplets, thereby forming particles. These particles then are separated from the drying gas and collected.

In scaling up such a spray drying process, for example from the laboratory or pilot plant scale to the commercial plant scale, certain problems may be encountered. If the drying rate and drying capacity are not adequately optimized undesirable problems may be faced such as improper drying of solvent particles, reduced product yield, purity etc. On the other hand increasing the drying rate that is inadequately scaled may result in unsuitable particle morphology and/or size distribution for some product particles, such as those having critically defined performance specifications. More significantly, it may also alter the way in which the solid-forming material precipitates as the solvent is evaporated, thereby changing the structure (e.g., porosity) of the particle to be out of specification standards, rendering the particle unable to properly contain and deliver a diagnostic or therapeutic agent.

There is therefore a need in the art for an improved spray-drying process that results in the production of homogenous solid amorphous dispersions at high purity with improved flow characteristics, improved content uniformity, and improved collection efficiency.

One of the objects of the present invention is to provide spray dried compositions of cation-insulin conjugate complexes involving a drying process that provides improved drying of particles without detrimentally impacting the product purity, yield and stability. The current process yields homogeneous spray dried solid particles of the target therapeutic agent that is further formulated with other requisite excipients to yield an oral pharmaceutical compositions of cation-insulin conjugate complexes.

Other objects and advantages of the present invention will be more fully apparent to those of ordinary skill in art, in light of the ensuing disclosure and appended claims.

OBJECTS OF THE INVENTION

The principal object of the present invention is to develop an orally administrable solid pharmaceutical composition of a cation-insulin conjugate complex comprising saturated or unsaturated $C_4$-$C_{12}$ fatty acids, fatty acid esters or salts thereof and at least three pharmaceutically acceptable excipients selected from the group comprising binders, disintegrants, diluents, lubricants, plasticizers, permeation enhancers and solubilizers.

Another object of the present invention is to develop an orally administrable solid pharmaceutical composition, wherein the oral dosage form is in the form of a tablet, capsule, particles, powder or sachet or dry suspensions.

Yet another object of the present invention is to develop a process for manufacturing an orally administrable solid pharmaceutical composition of a cation-insulin conjugate complex.

Still another object of the present invention is to develop a tablet composition of a cation-insulin conjugate complex.

Still another object of the present invention is to develop a dose of the orally administrable solid pharmaceutical composition, to achieve a maximum control of post prandial blood glucose concentration in diabetic patients within 5-60 minutes post-administration.

Still another object of the present invention is to develop a stable orally administrable pharmaceutical composition of a cation-insulin conjugate complex.

Still another object of the present invention is to develop a method for preparing amorphous spray-dried particles of a cation-insulin compound conjugate.

Still another object of the present invention is to develop a spray dried composition of IN-105.

Still another object of the present invention is to develop a pharmaceutical composition comprising the cation-peptide conjugate complex wherein the excipients do not impact the mitogenic potency of the conjugate.

STATEMENT OF THE INVENTION

Accordingly the present invention provides an orally administrable solid pharmaceutical composition of a cation-insulin conjugate complex comprising saturated or unsaturated $C_4$-$C_{12}$ fatty acids, fatty acid esters or salts thereof and at least three pharmaceutically acceptable excipients selected from the group comprising binders, disintegrants, diluents, lubricants, plasticizers, permeation enhancers and solubilizers; an orally administrable pharmaceutical composition, wherein the oral dosage form is in the form of a tablet, capsule, particles, powder or sachet or dry suspensions; a process for manufacturing an orally administrable solid pharmaceutical composition of a cation-insulin conjugate complex comprising saturated or unsaturated $C_4$-$C_{12}$ fatty acids or salts thereof and at least three pharmaceutically acceptable excipients selected from the group comprising binders, disintegrants, diluents, lubricants, plasticizers, permeation enhancers and solubilizers; a process for manufacturing an orally administrable solid pharmaceutical composition of a cation-insulin conjugate complex comprising saturated or unsaturated $C_4$-$C_{12}$ fatty acids or salts thereof and at least three pharmaceutically acceptable excipients selected from the group comprising binders, disintegrants, diluents, lubricants, plasticizers, solubilizers and permeation enhancers comprising the steps of a) grinding a suitable saturated or unsaturated $C_4$-$C_{12}$ fatty acids and/or salts of such fatty acid, b) Granulating the resulting fatty acid obtained from step (a) with an organic solvent, c) air-drying the granules obtained from step (b), d) rasping the dried granules through a mesh to obtain granules of desired particle size, e) blending the fatty acid granules with the cation-insulin conjugate complex with the other excipients, f) compressing the blended mixture for tablet formation; a process for manufacturing an orally administrable solid pharmaceutical composition of a cation-insulin conjugate complex, comprising saturated or unsaturated $C_4$-$C_{12}$ fatty acids or salts thereof and at least three pharmaceutically acceptable excipients selected from the group comprising binders, disintegrants, lubricants, plasticizers and permeation enhancers comprising the steps of a) Grinding suitable saturated or unsaturated $C_4$-$C_{12}$ fatty acids and/or salts of such fatty acid and a binder, b) suspending the cation-insulin conjugate complex in an organic solvent using the binder to form a wet mass, c) granulation of the components obtained from step (b) using the binder, d) Rasping the dried granules of step (c), e) blending the granules with other excipients, f) compressing the blended mixture for tablet formation; a process wherein the organic solvent used is selected from the group comprising isopropanol, acetone; methyl alcohol, methyl isobutyl ketone, chloroform, 1-propanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof; a 5-500 mg tablet composition of an cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; A 50 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; a 100 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; a 150 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; a 200 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; a 250 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers; a dose of the orally administrable solid pharmaceutical composition, to achieve a maximum control of post prandial blood glucose concentration in diabetic patients within 5-60 minutes post-administration; a stable orally administrable pharmaceutical composition of a cation-insulin conjugate complex comprising saturated or unsaturated $C_4$-$C_{12}$ fatty acids, fatty acid esters or salts thereof and at least three pharmaceutically acceptable excipients selected from the group comprising binders, disintegrants, diluents, lubricants, plasticizers, permeation enhancers and solubilizers characterized in that said composition remains stable over exposure to conditions selected from the group comprising (a) temperature range of about 2-40° C., (b) 25° C.±2° C./60%±5% relative humidity (RH), 30° C.±2° C./65%±5% relative humidity, 40° C.±2° C./75%±5% relative humidity, for over a period of at least 6 months, a method of preparing amorphous spray-dried particles of a cation-insulin compound conjugate said method comprising steps of a) Preparing a solution or suspension comprising the cation-insulin compound conjugate and a fatty acid component in a solvent, b) Spraying the solution into a chamber under conditions that allow for substantial amount of the solvent to be removed c) affording spray-dried particles of the cation-insulin compound conjugate; a spray-dried composition of IN-105; a spray-dried composition of IN-105, wherein the drug is substantially amorphous and homogeneous; a spray-dried composition of IN-105 with purity of at least 95%; a spray-dried composition of IN-105 with purity of at least 98%; a spray-dried composition of IN-105 with purity of at least 99%; an amorphous form of IN-105; an insulinotropic cation-peptide conjugate complex characterized in that said conjugate exhibits three-fold reduced mitogenicity in comparison to its native counterpart and a pharmaceutical composition comprising the cation-peptide conjugate complex comprising pharmaceutically acceptable excipients, said composition characterized in that the excipients do not impact the mitogenic potency of the conjugate.

BRIEF DESCRIPTION OF THE FIGURES

FIG. 1: Mean plasma insulin profile—IN-105 formulation tablets (FDT-3)
FIG. 2: Normalized glucose profile in administration of FDT-3
FIG. 3: Mean plasma insulin profile—IN-105 formulation tablets (FDT-19)
FIG. 4: Normalized glucose profile in administration of FDT-19
FIG. 5: Mean plasma insulin profile—IN-105 formulation tablets (FDT-20)
FIG. 6: Glucose profile after administration of FDT-20
FIG. 7: Plasma Insulin Profile
FIG. 8: Glucose Infusion Rate Profile
FIG. 9: Plasma Glucose Profile
FIG. 10: Parallelism and linearity of the bioassay across various concentrations of Insugen® and IN105 determined by the PLA software. The data represents average±SEM of triplicate values of an experiment.
FIG. 11: Mitogenic potency of Insugen compared with IN-105 and HIM-2 from PLA analysis using 4 points in a linear range.
FIG. 12: Parallelism and linearity of the bioassay across various concentrations of Insugen® versus IN105 (A) and Insugen versus HIM-2 (B) determined by the PLA software. The data represents average±SEM of triplicate values of an experiment.
FIG. 13: Mitogenic activity of IN-105 dialyzed compared with IN-105 powder for PLA analysis using a 4 points in a linear range.
FIG. 14: Comparison of Metabolic Potency between Insugen®, IN105 and HIM-2.
FIG. 15: Parallelism and linearity of the bioassay across various concentrations of Insugen® versus IN105 (A) and Insugen versus HIM-2 (B) determined by the PLA software. The data represents average±SEM of triplicate values of an experiment.
FIG. 16: One Site Competition Curves of (A) Insugen®, (B) IN105 and (C) HIM-2, respectively. The curves were determined by the Graph Pad version-4 software. The data represents average of triplicate values of an experiment.

DETAILED DESCRIPTION OF THE INVENTION

The present invention is in relation to an orally administrable solid pharmaceutical composition of a cation-insulin conjugate complex comprising saturated or unsaturated $C_4$-$C_{12}$ fatty acids, fatty acid esters or salts thereof and at least three pharmaceutically acceptable excipients selected from the group comprising binders, disintegrants, diluents, lubricants, plasticizers, permeation enhancers and solubilizers.

In another embodiment of the present invention, the cation-insulin conjugate complex is IN-105.

In yet another embodiment of the present invention, the fatty acid component is capric acid and/or lauric acid or salts thereof.

In still another embodiment of the present invention, the fatty acid is sodium caprate.

In still another embodiment of the present invention, the binder is selected from the group comprising polyvinylpyrrolidone, carboxymethylcellulose, methylcellulose, starch, gelatin, sugars, natural and synthetic gums or their combinations thereof.

In still another embodiment of the present invention, the binder is polyvinylpyrrolidone.

In still another embodiment of the present invention, the diluents is selected from the group comprising calcium salts, cellulose or cellulose derivatives, palatinose, organic acids, sugar and sugar alcohols, pectate salts or combinations thereof.

In still another embodiment of the present invention, the diluent is mannitol.

In still another embodiment of the present invention, the disintegrant is selected from the group comprising cross-linked polyvinylpyrrolidone, carboxymethylcellulose, methyl cellulose, cation-exchange resins, alginic acid, guar gum or their combinations thereof.

In still another embodiment of the present invention, the lubricant is selected from the group comprising magnesium stearate, sodium stearate, sodium benzoate, sodium acetate, fumaric acid, polyethyleneglycols, alanine and glycine.

In still another embodiment of the present invention, the lubricant is magnesium stearate.

In still another embodiment of the present invention, the permeation enhancer is selected from the group comprising sodium lauryl sulfate, sodium laurate, palmitoyl carnitine, phosphatidylcholine, cyclodextrin and derivatives thereof, carnithine and their derivatives, mucoadhesive polymers, zonula occludins toxin, bile salts, fatty acids or combinations thereof.

In still another embodiment of the present invention, the permeation enhancer is sodium lauryl sulphate.

In still another embodiment of the present invention, the permeation enhancer is beta-cyclodextrin.

In still another embodiment of the present invention, the plasticizer is selected from the group comprising polyethyleneglycol, propylene glycol, acetyl citrate, triacetin, acetylated monoglyceride, rape oil, olive oil, sesame oil, acetyltriethyl citrate; glycerin sorbitol, diethyloxalate, diethylmalate, diethylfumarate, dibutylsuccinate, dibutyl phthalate, dioctylphthalate, dibutylsebacate, triethylcitrate, tributylcitrate, glyceroltributyrate, glyceryl triacetate, or mixtures thereof.

In still another embodiment of the present invention, the plasticizer is polyethyleneglycol.

The present invention is also in relation to an orally administrable pharmaceutical composition wherein the oral dosage form is in the form of a tablet, capsule, particles, powder or sachet or dry suspensions.

The present invention is also in relation to a process for manufacturing an orally administrable solid pharmaceutical composition of a cation-insulin conjugate complex comprising saturated or unsaturated $C_4$-$C_{12}$ fatty acids or salts thereof and at least three pharmaceutically acceptable excipients selected from the group comprising binders, disintegrants, diluents, lubricants, plasticizers, permeation enhancers and solubilizers.

The present invention is also in relation to a process for manufacturing an orally administrable solid pharmaceutical composition of a cation-insulin conjugate complex of claim 18, comprising saturated or unsaturated $C_4$-$C_{12}$ fatty acids or salts thereof and at least three pharmaceutically acceptable excipients selected from the group comprising binders, disintegrants, diluents, lubricants, plasticizers, solubilizers and permeation enhancers comprising the steps of a. Grinding a suitable saturated or unsaturated $C_4$-$C_{12}$ fatty acids and/or salts of such fatty acid.

b. Granulating the resulting fatty acid obtained from step (a) with an organic solvent c. Air-drying the granules obtained from step (b).

d. Rasping the dried granules through a mesh to obtain granules of desired particle size.

e. Blending the fatty acid granules with the cation-insulin conjugate complex with the other excipients.

f. Compressing the blended mixture for tablet formation.

The present invention is also in relation to a process for manufacturing an orally administrable solid pharmaceutical composition of a cation-insulin conjugate complex of claim 18, comprising saturated or unsaturated $C_4$-$C_{12}$ fatty acids or salts thereof and at least three pharmaceutically acceptable excipients selected from the group comprising binders, disintegrants, lubricants, plasticizers and permeation enhancers comprising the steps of a) Grinding suitable saturated or unsaturated $C_4$-$C_{12}$ fatty acids and/or salts of such fatty acid and a binder.

b) Suspending the cation-insulin conjugate complex in an organic solvent using the binder to form a wet mass.

c) Granulation of the components obtained from step (b) using the binder.

d) Rasping the dried granules of step (d).

e) Blending the granules with other excipients.

f) Compressing the blended mixture for tablet formation.

In still another embodiment of the present invention the organic solvent used is selected from the group comprising isopropanol, acetone, methyl alcohol, methyl isobutyl ketone, chloroform, 1-propanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

The present invention is also in relation to a 5-500 mg tablet composition of an cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a 50 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a 100 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a 150 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a 200 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a 250 mg tablet composition of an a cation-insulin conjugate complex comprising saturated or unsaturated $C_4$-$C_{12}$ fatty acids, fatty acid esters, or salts thereof and at least three pharmaceutically acceptable excipients selected from the group comprising binders, disintegrants, lubricants, plasticizers and permeation enhancers.

The present invention is also in relation to a dose of the orally administrable solid pharmaceutical composition to achieve a maximum control of post prandial blood glucose concentration in diabetic patients within 5-60 minutes post-administration.

In another embodiment of the present invention, the orally administrable solid pharmaceutical composition according to of any of the preceding claims, which produces a lowered serum glucose in human patients by at least 5% with in 120 minutes post oral administration.

The present invention is also in relation to a stable orally administrable pharmaceutical composition of a cation-insulin conjugate complex comprising saturated or unsaturated $C_4$-$C_{12}$ fatty acids, fatty acid esters or salts thereof and at least three pharmaceutically acceptable excipients selected from the group comprising binders, disintegrants, diluents, lubricants, plasticizers, permeation enhancers and solubilizers characterized in that said composition remains stable over exposure to conditions selected from the group comprising (a) temperature range of about 2-40° C.

(b) 25° C.±2° C./60%±5% relative humidity (RH), 30° C.±2° C./65%±5% relative humidity, 40° C.±2° C./75%±5% relative humidity for over a period of at least 6 months.

In another embodiment of the present invention, the impurities do not increase by more than 5% when compared to the impurity levels at the time of manufacture.

In still another embodiment of the present invention, the impurities do not increase by more than 10% when compared to the impurity levels at the time of manufacture.

In still another embodiment of the present invention, the assay of said compound in the composition do not decrease by more than 10%.

In still another embodiment of the present invention, the dissolution profile is at least 75% at any said time interval.

In still another embodiment of the present invention, the time interval ranges for a period over 2 years.

In still another embodiment of the present invention, the difference between the hardness profile is no more than 1 kg/cm² when compared to the hardness profile at the time of manufacture.

In still another embodiment of the present invention, at least 95%±2% of the composition remains undegraded over exposure to conditions selected from the group comprising (a) temperature range of about 2-8° C. or 25° C.-40° C.

(b) 25° C.±2° C./60%±5% relative humidity (RH), 30° C.±2° C./65%±5% relative humidity, 40° C.±2° C./75%±5% relative humidity for over a period of at least 6 months.

In still another embodiment of the present invention, at least 90%±2% of the composition remains undegraded over exposure to conditions selected from the group comprising
   (a) temperature range of about 2-8° C. or 25° C.-40° C.
   (b) 25° C.±2° C./60%±5% relative humidity (RH), 30° C.±2° C./65%±5% relative humidity, 40° C.±2° C./75%±5% relative humidity for over a period of at least 6 months.

The present invention is also in relation to a method of preparing amorphous spray-dried particles of a cation-insulin compound conjugate said method comprising steps of
   a. Preparing a solution or suspension comprising the cation-insulin compound conjugate and a fatty acid component in a solvent.
   b. Spraying the solution into a chamber under conditions that allow for substantial amount of the solvent to be removed
   c. Affording spray-dried particles of the cation-insulin compound conjugate.

In still another embodiment of the present invention, the fatty acid component is selected from a group comprising C4-C12 fatty acid and/or salts of such a fatty acid.

In still another embodiment of the present invention, the fatty acid component is sodium caprate.

In still another embodiment of the present invention, the cation-insulin compound conjugate is IN-105.

In still another embodiment of the present invention, the solvent is water.

In still another embodiment of the present invention, the solution or suspension containing the cation-insulin conjugate and a fatty acid component in a solvent further comprises a diluent.

In still another embodiment of the present invention, the diluent is mannitol.

In still another embodiment of the present invention, the size of the spray-dried particles is about 1-100μ.

In still another embodiment of the present invention, the solution or suspension comprising the cation-insulin conjugate is spray-dried at a temperature ranging between 80° C.-150° C.

In still another embodiment of the present invention, the atomization pressure employed for spray drying is in the range of 0.5 kg/cm2 to 1.5 kg/cm2.

In still another embodiment of the present invention, purity of the spray-dried composition of a cation-insulin compound conjugate is at least 95%.

In still another embodiment of the present invention, purity of the spray-dried composition of a cation-insulin compound conjugate is at least 98%.

In still another embodiment of the present invention, purity of the spray-dried composition of a cation-insulin compound conjugate is at least 99%.

The present invention is in relation to a spray-dried composition of IN-105.

The present invention is also in relation to a spray-dried composition of IN-105, wherein the drug is substantially amorphous and homogeneous.

The present invention is also in relation to a spray-dried composition of IN-105 with purity of at least 95%.

The present invention is in relation to a spray-dried composition of IN-105 with purity of at least 98%.

The present invention is also in relation to a spray-dried composition of IN-105 with purity of at least 99%.

The present invention is also in relation to an amorphous form of IN-105.

The present invention is also in relation to an insulinotropic cation-peptide conjugate complex characterized in that said conjugate exhibits three-fold reduced mitogenicity in comparison to its native counterpart.

In still another embodiment of the present invention conjugate reduces in-vitro and/or in-vivo cell proliferation to at least 20%±5% that of its native counterpart.

In still another embodiment of the present invention conjugate reduces in-vitro and/or in-vivo cell proliferation to least 2%±0.5% that of its native counterpart.

In still another embodiment of the present invention said conjugate displays similar metabolic efficiency as that of its native counterpart.

The present invention is also in relation to a pharmaceutical composition comprising the cation-peptide conjugate complex, comprising pharmaceutically acceptable excipients, said composition characterized in that the excipients do not impact the mitogenic potency of the conjugate.

The primary object of the invention is to provide an immediate release formulation comprising proteins/peptides, their conjugates, and/or cation-polypeptide conjugate complexes demonstrating desirable pharmacokinetic profiles and potency in efficacy models of diabetes in humans upon oral delivery. The current state of the art recognizes the instability of unmodified insulin in the gastrointestinal tract and has endeavored to circumvent these problems by developing a rationally designed formulation for immediate release.

The cation-peptide conjugate complexes, cation-insulin conjugate complexes of the present invention are characterized to demonstrate reduced mitogenic potencies. The conjugates described in the present invention are advantageous due to the fact that there is relatively lesser or no risk of induction of mitogenic reactions even after long term use and hence may be safely used for long term therapy and management of diabetes. The therapeutic compounds of the present invention are characterized to demonstrate three fold reduced mitogenic potency when compared to Insugen®.

According to one significant aspect of the present invention, the excipients in the drug product do not impact the mitogenic characteristics of the drug substance and hence the formulation or composition remains relatively less mitogenic potency when compared to the currently marketed insulin therapeutics.

Another objective of the present invention is to provide an immediate release formulation comprising protein/peptides, their conjugates, and/or cation-polypeptide conjugate complexes displaying stability across a range of temperatures for time intervals extending up to 12 months. The currently developed formulation is stable at room temperature and also exhibits stability at elevated temperatures.

According to one aspect of the invention the pharmaceutical composition so manufactured is evaluated at different test conditions of temperatures and relative for time interval extending up to 12 months.

A preferred embodiment of the present invention relates to orally deliverable formulation comprising 0.01%-20% w/w of insulin, insulin compound conjugates and/or cation insulin conjugates, 10%-60% w/w of one or more fatty acid components selected from saturated or unsaturated C4-C12 fatty acids and/or salts of such fatty acids, 10%-60% w/w of a diluent, 1%-20% of disintegrant, 0.01%-5% of binder and 0.01%-5% of adsorbent including but not limited to other suitable pharmaceutically acceptable carriers.

Accordingly, one aspect the invention relates to a formulation comprising at least one biologically active compound selected from derivatized insulin conjugates, insulin analogues, insulin complexes including but not limited to other therapeutic agents with insulin-like activity.

In yet another aspect, the invention provides a process of manufacturing the above mentioned orally deliverable formulations under optimal operational conditions with suitable excipients that enhance resistance of the therapeutically active agent to degradation.

In yet another preferred aspect, the process of manufacture of the orally deliverable tablet comprising at least one biologically active compound selected from proteins/peptides, their conjugates, and/or cation-polypeptide conjugate complexes possessing resistance to enzymatic degradation comprising the steps:

1. Grinding a suitable saturated or unsaturated C4-C12 fatty acid and/or salts of such a fatty acid.
2. Granulating the resulting fatty acid obtained from step (1) with an organic solvent.
3. Air-drying the granules obtained from step (2).
4. Rasping the dried granules through a mesh to obtain granules of desired size of about 250 μm.
5. Blending the fatty acid granules, cation-insulin compound conjugate with other excipients.
6. Compressing the blended mixture for tablet formation.

In accordance with the above objects and others, the invention is directed in part to an oral solid dosage form comprising a dose of modified insulin which achieves a maximum control of post prandial blood glucose concentration in diabetic patients within 20-30 minutes post-administration.

Those of skill will readily appreciate that dose levels can vary as a function of the specific compound, the severity of the symptoms and the susceptibility of the subject to side effects. Preferred dosages for a given compound are readily determinable by those of skill in the art by a variety of means. A preferred means is to measure the physiological potency of a given compound. The dosage unit form may be a liquid or a solid, such as a tablet, capsule or particles, including a powder or sachet.

The instant invention also relates to an improvised process of spray drying resulting in the production of spray dried particles of 1-100 g containing the therapeutic drug with at least one of pharmaceutically acceptable excipient.

The process involves (a) the preparation of a solution which contains therapeutic drug and optionally a diluent of concentration between 0.001% and 20% w/w, optionally 10%-60% w/w of one or more fatty acid components selected from saturated or unsaturated C4-C12 fatty acids and/or salts of such fatty acids (b) spray drying the resulting slurry to form a spray dried powder.

Subsequent aspect of the invention relates to combining the other pharmaceutical excipient with the spray dried powder that is compressed into a tablet form.

Methods of the invention can provide, For e.g., the ability to generate homogenous solid particles with therapeutic agent given the conditions are conducive to provide increased evaporation efficiency per given heat input. The method of preparing such powdered particles in the invention can comprise, for example, preparing an aqueous suspension or solution of a bioactive material forming a mixture of the solution or suspension, spraying ultrafine droplets by depressurizing the mixture, and drying the droplets into powdered particles by exchanging the spray gases with drying gases, e.g., to by spraying into a drying chamber of the spray dry apparatus.

Other objects and advantages of the present invention will be more fully apparent to those of ordinary skill in art, in light of the ensuing disclosure and appended claims.

The invention further provides a method of treatment of diabetes, impaired glucose tolerance, early stage diabetes, and late stage diabetes in animals, preferably humans, and a method of achieving glucose homeostasis, comprising administering one or more unit doses of the dosage forms an immediate release formulation comprising proteins/peptides, their conjugates, and/or cation-polypeptide conjugate complexes with suitable excipients that enhance resistance of the therapeutically active agent to degradation.

DEFINITIONS

In describing and claiming the present invention, the following terminology will be used in accordance with the definitions set out herein.

The "cation-insulin compound conjugate" includes any insulin compound component. The insulin compound may, for example, be a mammalian insulin compound, such as human insulin, or an insulin compound derivatives or analogs. The therapeutic agent specifically relates to the molecule IN-105. IN-105 is an insulin molecule conjugated at the epsilon amino acid Lysine at position B29 of the insulin B-chain with an amphiphilic oligomer of structural formula $CH_3O-(C_4H_2O)_3-CH_2-CH_2-COOH$. The molecule may be monoconjugated at A1, B1 and B29, di-conjugated at various combinations of A1, B1 and B29, or triconjugated at various combinations of A1, B1 and B29.

"Therapeutically effective amount" refers to an amount of insulin included in the dosage forms of the invention which is sufficient to achieve a clinically relevant control of blood glucose concentrations in a human diabetic patient either in the fasting state or in the fed state effective, during the dosing interval.

As used herein, "disintegrators" or "disintegrants" are substances that facilitate the breakup or facilitate disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "binders" are agents used to impart cohesive qualities to the powdered material. Binders, or "granulators" as they are sometimes known, impart cohesiveness to the tablet formulation, which insures the tablet remaining intact after compression, as well as improving the free-flowing qualities by the formulation of granules of desired hardness and size. Materials commonly used as binders include carboxymethylcellulose, methylcellulose, polyvinylpyrrolidone, starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, Veegum, microcrystalline cellulose, microcrystalline dextrose, amylose, and larch arabogalactan, and the like. Polyvinylpyrolidone is used in context of the present invention.

As used herein, "disintegrators" or "disintegrants" are substances that facilitate the breakup or facilitate disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked lyvinpoylpyrrolidone, carboxymethylcellulose, and the like.

"Lubricant" may be selected from the group comprising magnesium stearate, sodium stearate, sodium benzoate, sodium acetate, fumaric acid, polyethyleneglycols (PEG)

higher than 4000, alanine and glycine. Preferred lubricant in context of the present invention is magnesium stearate or sodium stearate.

"Magnesium stearate" means a compound of magnesium with a mixture of solid organic acids obtained from fats, and chiefly consists of variable proportions of magnesium stearate and magnesium palmitate. It is used as a pharmaceutical necessity (lubricant) in the manufacture of compressed tablets.

"Permeation enhancers" means any compound that increases membrane permeability and facilitate drug transport through the biological membrane, thereby improving the bioavailability of the delivered therapeutic agent. Suitable membrane-permeation enhancers include surfactants such as sodium lauryl sulfate, sodium laurate, palmitoyl carnitine, Laureth-9, phosphatidylcholine, cyclodextrin and derivatives thereof, bile salts such as sodium glycochlate, sodium deoxycholate, sodium taurocholate, and sodium fusidate, chelating agents including EDTA, citric acid and salicylates, and fatty acids (e.g., oleic acid, lauric acid, acylcarnitines, mono- and diglycerides), L-carnitine and derivatives, muco-adhesive polymers, ZOT (zonula occludans toxin) or combinations thereof.

"Plasticizers" which are selected from the group consisting of acetyl citrate, triacetin, acetylated monoglyceride, rape oil, olive oil, sesame oil, acetyltriethyl citrate, glycerin sorbitol, diethyloxalate, diethylmalate, diethylfumarate, dibutylsuccinate, dibutyl phthalate, dioctylphthalate, dibutylsebacate, triethylcitrate, tributylcitrate, glyceroltributyrate, glyceryl triacetate, polyethyleneglycol, propylene glycol, and mixtures thereof. The plasticizer is most preferably polyethylene glycol. The plasticizer may be present up to 40% w/w of the film forming polymer. Representative plasticizer used in context of the present invention is PEG (polyethylene glycol)

"Polyalkylene glycol" or "PAG" refers to substituted or unsubstituted, linear or branched polyalkylene glycol polymers such as polyethylene glycol (PEG), polypropylene glycol (PPG), and polybutylene glycol (PBG), and combinations thereof (e.g., linear or branched polymers including combinations of two or more different PAG subunits, such as two or more different PAG units selected from PEG, PPG, PPG, and PBG subunits), and includes the monoalkylether of the polyalkylene glycol. The term PAG subunit means a single PAG unit, e.g., "PEG subunit" refers to a single polyethylene glycol unit, e.g., —(CH2CH2O)—, "PPG subunit" refers to a single polypropylene glycol unit, e.g., —(CH2CH2CH2O)—, and "PBG subunit" refers to a single polypropylene glycol unit, e.g., —(CH2CH2CH2CH2O)—. PAGs and/or PAG subunits also include substituted PAGs or PAG subunits, e.g., PAGs including alkyl side chains, such as methyl, ethyl or propyl side chains, or carbonyl side chains, as well as PAGs including one or more branched PAG subunits, such as iso-PPG or iso-PBG.

"Solubilizers" may be any substance that enhances the aqueous solubility of a drug.

As used herein, "pharmaceutically acceptable carrier" comprises one or several agents selected from the group consisting of carbohydrates and modified carbohydrates and derivatives thereof, polyethylene and/or polypropylene glycol and derivatives thereof, inorganic fillers or lubricating agents, fatty acids and their esters and salts, preservatives and coating agents.

As referred in the specification "effective amount" means an amount of any agent that is nontoxic but sufficient to provide the desired local or systemic effect and performance at a reasonable benefit/risk ratio attending any medical treatment. For example, an effective amount of a lubricant is an amount sufficient to function for lubricating the composition for tableting purposes without providing any detrimental effects.

In context of the present invention "organic solvents" refers to any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

"Assay" may be laboratory test to find and measure the amount of a specific substance.

"Impurities" may be defined as components not part of the native formulation that cause the quality or condition of the composition to impure, essentially attributed by one or a combination of any of the following characteristics:

a. Contamination or pollution.

b. Lack of consistency or homogeneity; adulteration.

c. Something that renders something else impure; an inferior component or additive.

The "dissolution test" is provided to determine compliance with the dissolution requirements as stated in the individual monograph for a tablet or capsule dosage form. Tablet dissolution is a standardized method for measuring the rate of drug release from a dosage form. The principle function of the dissolution test may be summarized with attributes such as a) Optimisation of therapeutic effectiveness during product development and stability assessment b) Routine assessment of production quality to ensure uniformity between production lots c) Assessment of "bioequivalence", that is to say, production of the same biological activity from discrete batches of products from one or different manufacturers.

Dissolution can be carried out by dissolving the tablet in a optimal volume of a medium at about 37.0±0.5° C. and with a rotation speed of about 50 rpm. Dissolution is measured at various time intervals starting 15 minutes. The various media that may be used for carrying out the dissolution tests include water, buffer and acidic media with pH ranging from 1-9, more preferably in the range of 2-7.

"Hardness" is generally measured as the force required to break a tablet in a diametrial compression test. The test consists of placing the tablet between two anvils until the tablet breaks. The crushing strength that causes the tablet to break is recorded. "Hardness" is sometimes referred as the tablet crushing strength. Several instruments used for measuring tablet hardness include Stokes (Monsanto) tester, the strong-Cobb tester, the Pfizer tester, the Erweka tester, the Heberlein tester (or Schleuniger) tester, the key tester and the van der Kamp tester. The unit for measuring hardness is $Kg/cm^2$ "Disintegration" is defined as that state in which any residue of the unit, except fragments of insoluble coating or capsule shell, remaining on the screen of the test apparatus is a soft mass having no palpably firm core.

The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50

Chem. Eng. Prog. Monogram. Series 2 (1954), and Masters, Spray Drying Handbook (Fourth Edition 1985).

As used herein, the term "drying" in reference to droplets or particles formed as the result of removal of the solvent from the droplet or particle.

As used herein, the term "particle" includes micro-, sub-micro-, and macro-particles. Generally, the particles are between about 100 nm and 5 mm in diameter or longest dimension. The particles can be spheres, capsules, irregular shapes, crystals, powders, agglomerates, or aggregates.

The invention contemplates use of coating agents which may include both non-functional (insta-coat, kollicoat IR) or enteric coating agents such as cellulose based polymers, film coating agents or polymethyl acrylate and other coating agents known to a person of ordinary skill in the art.

The present invention relates in one broad compositional aspect to formulations including covalently conjugated therapeutic agent complexes wherein the therapeutic agent is covalently bonded to one or more molecules of a polymer incorporating as an integral part of said polymer a hydrophilic moiety, e.g., a polyalkylene glycol moiety, and a lipophilic moiety, e.g., a fatty acid moiety. In one preferred aspect, the therapeutic agent may be covalently conjugated by covalent bonding with one or more molecules of a linear polyalkylene glycol polymer incorporated in which, as an integral part thereof is a lipophilic moiety, e.g., a fatty acid moiety.

The modified insulin conjugates as used in the present invention are developed by attaching low-molecular-weight polymers or oligomers, that are amphiphilic in nature comprising a polyethylene glycol portion which is hydrophilic while the alkyl chain is lipophilic. The attachment modifies the solubility of the drug molecule and stabilizes the protein or peptide from enzymatic degradation in the gastrointestinal tract. The conjugated drug is absorbed more efficiently across the GI wall than the drug in its native state. On traversing to the blood stream the bond between the hydrophilic and hydrophobic chain is hydrolyzed leaving the highly active insulin-PEG compound circulating in the blood thus favorably altering the pharmacokinetics of the drug.

The present invention specifically relates to the molecule IN-105. IN-105 is an insulin molecule conjugated at the epsilon amino acid Lysine at position B29 of the insulin B-chain with an amphiphilic oligomer of structural formula $CH_3O$—$(C_4H_2O)_3$—$CH_2$—$CH_2$—$COOH$.

As per one of the most important aspects of the present invention, the cation-peptide conjugate complexes, cation-insulin conjugate complexes of the present invention are characterized to demonstrate reduced mitogenic potencies. The conjugates described in the present invention are advantageous due to the fact that there is relatively lesser or no risk of induction of mitogenic reactions even after long term use and hence may be safely used for long term therapy and management of diabetes. The therapeutic compounds of the present invention are characterized to demonstrate three fold reduced mitogenic potency when compared to Insugen®.

According to one significant aspect of the present invention, the excipients in the drug product do not impact the mitogenic characteristics of the drug substance and hence the formulation or composition remains relatively less mitogenic potency when compared to the currently marketed insulin therapeutics.

"Native counterparts" refer to the un-modified peptide/protein displaying similar basic in-vitro or in-vivo bioactivity as that of the modified counterpart, ie., said molecule is the peptide/polypeptide prior to being subject to any kind of modification.

According to standard terminology, the term "mitogenic" define those substances that stimulate the division of cells which would otherwise (i.e., without the influence of this substance) have very limited division.

The inventive merit of the substance presented in the instant invention is revealed in the fact that, with reference to specific experiences and experiments, experts believe that insulin as a substance in itself was considered to be mitogenic [DeMeyts P; The structural basis of Insulin and Insulin-like growth factor-1 receptor binding and negative cooperativity and its relevance to Mitogenic versus metabolic signaling. Diabetologia 37: S135-S148, 1994], Ish-Shalom D, Christoffersen C T, Vorwerk P, Sacerdoti-Sierra N, Shymko R M, Naor D and De Meyts P; Mitogenic properties of Insulin and Insulin analogues mediated by the insulin receptor. Diabetologia 40: S25-S31 and the protein/peptides, their conjugates, and/or cation-polypeptide conjugate complexes of the present invention display three fold decreased mitogenic potency determined by in-vitro induction of measurable proliferation of Balb 3T3-A31 cells.

According to one aspect of the present invention, exemplary compounds of the instant invention are said to exhibit "reduced mitogenicity" as compared to Insugen® if it induces detectably lower levels of cell proliferation as measured by Alamar blue dye uptake by the cells. Those skilled in the art will recognize that other suitable methods that may be used and that the invention is in no way limited to a specific proliferation assay.

According to one aspect of the present invention, exemplary compounds of the instant invention are said to be substantially "non-mitogenic" as compared to Insugen® if it induces undetectably lower levels of cell proliferation as measured by Alamar blue dye uptake by the cells. Those skilled in the art will recognize that other suitable methods may be used and that the invention is in no way limited to a specific proliferation assay.

Colorimetric in-vitro bioassays were employed to quantitate mitogenic activity [Okajima T., Nakamura K., Zhang H., Ling N., Tanabe T., Yasuda T., and Rosenfeld R. G. Sensitive Colorimetric Bioassays for Insulin-like Growth Factor (IGF) Stimulation of Cell Proliferation and Glucose Consumption: Use in Studies of IGF Analogs. Endocrinology, 1992, Vol. 120: 2201-2210.]

Biological assays are frequently analyzed with the help of the parallel-line method. The logarithm of the doses are plotted on the horizontal axis, whereas the corresponding responses are represented on the vertical axis. The individual responses for each treatment are symbolized by the blue triangles for the standard preparation and by the green squares for the sample preparation.

With the help of the parallel-line model the statistical validity of the following hypotheses is tested:
1. The dose-response relationship is linear for the standard and sample preparation.
2. The dose-response curve has a significant slope.
3. The dose-response curves of the standard and sample preparation are parallel.

The parallel-line procedure has several advantages compared to traditional single-point assay. Due to the check of the hypotheses mentioned above
1. a linear dose-response correlation is not only assumed but also proven
2. a dose-independent relative potency is obtained.

The reproducibility of the mitogenic potencies was analyzed by utilizing the 4-parameter logistics' curve fit, on the linear portion of the curve consisting of at least four consecutive points. The results showed 3 folds statistically lesser mitogenic potencies of IN105 compared to Insugen®.

As per one significant aspect of the invention the mitogenic potency of the IN-105 molecule in the powdered form and dialyzed solution are the same. IN-105 is three folds less mitogenic when compared to Insugen®.

As per yet another significant aspect of the invention the mitogenic potency of the HIM2 molecule is thirty folds lesser when compared to Insugen®.

Without limitation, exemplary derivatives eg. IN-105 of the instant invention reduce in-vitro cell proliferation to at least 20%, or at least 25%, or at least 30% at least 35%, at least 40% to that of their native counterparts. More preferably, to the level of at least 30%.

Without limitation, exemplary derivatives eg. HIM-2 of the instant invention reduce in-vitro cell proliferation to at least 2%, or at least 2.5%, or at least 3%, at least 3.5% to that of their native counterparts. More preferably, to the level of at least 3.8%, most preferably to at least 4%.

According to yet another aspect of the present invention, evaluation of insulin binding to its cognate receptor is conducted to compare the relative binding affinities of the drug substance form Insugen®, IN-105 and HIM-2. The most significant aspect of the invention relates to the fact that the metabolic activity of exemplary compounds of the present invention remain unaffected and uncompromised notwithstanding the considerable reduction in mitogenic potency in comparison to their native counterparts.

The effect of insulin on the cells as metabolic action is dependant on the ability of insulin to bind to insulin receptor and the metabolic assay exemplified in the present invention helps determine the effect of insulin on glucose uptake by differentiated adipocytes, thereby provide data for evaluation and comparison of the metabolic efficiency of the exemplary drug substances of the instant invention.

Extraction of Drug Substance from Drug Product:

Insugen® and exemplary compounds of the instant invention eg. IN105 and HIM2 would be used for preparing Zn free and excipient free drug substance. The vials would be clarified using glacial acetic acid (pH ~3.4). The clarified solution will be loaded on the C8 silica reverse phase column and separated using a gradient elution with 250 mM acetic acid and 100% ethanol. Fractions would be collected during elution, and pooled based on greater than or equal to 99% purity. This elution pool will be dialyzed for 15 hrs using a 1 KD cutoff membrane against 10 mM Tris, pH 8.0. Finally, dialysed Zn free and excipient free insulin, obtained at pH 8.0, will be analyzed by analytical RP-HPLC.

HepG2 cells were obtained from ATCC. Dulbecco's Modified Eagle's medium (DMEM), Heat Inactivated Fetal Bovine Serum (FBS), 100× Penicillin-Streptomycin solution and 100×HEPES salt solution were procured from Invitrogen. Bovine serum albumin, Sodium hydroxide, Triton-X 100 and Sodium bicarbonate was obtained from Sigma Aldrich.

The radiolabeled recombinant human Insulin would be procured from Immunotech (Beckman Coulter) with a specific radioactivity of 2200 Ci/mmole (Catalog No. A36474)

Methods:

HepG2 cells are maintained in 10 mM HEPES-buffered DMEM supplemented with 10% FBS and 1× Penicillin-Streptomycin solution under humidified conditions at 37° C. in an atmosphere of 5% CO2. For the assay, HepG2 cells are trypsinized and seeded at a density of 400,000 cells per well of a 24 well plate. After 3 days of incubation the cells are used to perform the radio-ligand binding assays (1, 2).

Prior to performing the assay the media is removed and the cells are washed twice with the Binding buffer (DMEM, 2.2 mg/ml Sodium bicarbonate, 1 mg/ml Bovine Serum albumin and 50 mM HEPES) to remove any traces of growth factors present in the medium. The competitive binding experiments are set up in duplicates using the fixed amount of radioligand (0.325 nM) and varying concentrations of cold Insulin drug substance (from 10-13 M to 10-5 M). The final reaction volume is made to 1 ml. The plates are then incubated at 15° C. overnight with shaker set at 60 rpm (2). The following day all the media from the wells are discarded and each well is washed twice with ice-cold binding buffer.

Each well received 1 ml of solubilization reagent (0.5 M Sodium hydroxide, 0.5% Triton-X 100). The solubilized cell pellets are transferred to a Radioimmunoassay tube and the bound radioactivity was read in a gamma counter (Stratec BioMedical Systems, Germany) The instrument is calibrated and found to have an efficiency of 80%.

Binding Affinity calculations: For normalization of the Counts per minute (CPM values) at various concentrations of insulin used, percentage binding was calculated using the following equation;

% Bound=(CPMsample−CPMblank)/(CPMcontrol−CPMblank)×100.

Where CPMcontrol is the average CPM of the wells which contained cells with radiolabeled Insulin without any cold Insulin added, CPMblank is the average CPM of the wells which did not contain radiolabeled Insulin as well as cold insulin and CPMsample was the average CPM of the wells which contained radiolabeled Insulin as well as varying concentrations of cold Insulin.

Analysis of Competitive Binding Curves:

Competitive binding experiments measure the binding of a single concentration of labeled ligand in the presence of various concentrations of unlabeled ligand. Competitive binding experiments are used to determine receptor number and affinity by using the same compound as the labeled and unlabeled ligand.

The experiment is done with a single concentration of radio ligand. The incubation should occur until equilibrium has been reached, typically, varying concentrations of unlabeled compound spanning about six orders of magnitude.

The top of the curve is a plateau at a value equal to radio ligand binding in the absence of the competing unlabeled drug. This is total binding. The bottom of the curve is a plateau equal to nonspecific binding (NS). The difference between the top and bottom plateaus is the specific binding.

The Y axis can be expressed as cpm or converted to more useful units like fmol bound per milligram protein or number of binding sites per cell. It is possible to normalize the data from 100% (no competitor) to 0% (nonspecific binding at maximal concentrations of competitor).

The concentration of unlabeled drug that results in radio ligand binding halfway between the upper and lower plateaus is called the IC 50 (inhibitory concentration 50%) also called the EC 50 (effective concentration 50%). The IC50 is the concentration of unlabeled drug that blocks half the specific binding.

If the labeled and unlabeled ligand competes for a single binding site, the steepness of the competitive binding curve is determined by the law of mass action.

Nonlinear regression is used to fit the competitive binding curve to determine the log (IC50). Typically the Graph pad Prism Software is used and using the One Site Competition model equation, the Log(IC50) is determined.

In order to determine the best-fit value of IC 50 (the concentration of unlabeled drug that blocks 50% of the specific binding of the radio ligand), the nonlinear regression problem must be able to determine the 100% (total) and 0% (nonspecific) plateaus. With data collected over wide range of concentrations of unlabeled drug, the curve will have clearly defined bottom and top plateaus and the program should have no trouble fitting all three values (both plateaus and the IC 50).

The rationally formulated composition is bioavailable upon immediate release. In associatively conjugated therapeutic agent of the above-described type, the polymer component may be suitably constructed, modified, or appropriately functionalized to impart the ability for associative conjugation in a selective manner.

In one aspect, the invention provides fatty acid compositions with one or more saturated or unsaturated C4, C5, C6, C7, C8, C9 or C10 fatty acids and/or salts of such fatty acids. Preferred fatty acids are caprylic, capric, myristic and lauric. Preferred fatty acid salts are sodium salts of caprylic, capric, myristic and lauric acid.

The modifying moieties may include other hydrophilic polymers. Examples include poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like. The polymers can be homopolymers or random or block copolymers and terpolymers based on the monomers of the above polymers, linear chain or branched.

The total amount of cation-insulin compound conjugate to be used can be determined by those skilled in the art. The amount of therapeutic agent is an amount, effective to accomplish the purpose of the particular active agent. The amount in the composition is a therapeutically effective dose, i.e., a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

In certain preferred embodiments, the pharmaceutical composition contained in one or more dosage forms comprises from about 5 mg to about 800 mg of delivery agent, preferably about 10 mg to about 600 mg, more preferably from about 10 mg to about 400 mg, even more preferably from about 25 mg to about 200 mg, most preferably about 75 mg, 100 mg or 150 mg. More preferably, the composition provides a peak plasma insulin concentration within about 15 minutes to about 60 minutes after oral administration and more preferably within about 10-20 minutes after oral administration to fed diabetic patients.

It is contemplated for purposes of the present invention that dosage forms of the present invention comprising therapeutically effective amounts of insulin may include one or more unit doses (e.g., tablets, capsules, powders, semisolids, oral sprays, sublingual tablets (e.g. gelcaps or films) to achieve the therapeutic effect. It is further contemplated for the purposes of the present invention that a preferred embodiment of the dosage form is an oral dosage form.

In some cases, the complexed insulin compound conjugate will exhibit an extended or otherwise altered pK profile relative to a scientifically acceptable control, such as a corresponding uncomplexed insulin compound conjugate. pK profile can be assessed using standard in vivo experiments, e.g., in mice, rats, dogs, or humans. Assays described herein for assessing the attributes of cation-insulin compound conjugate complexes are an aspect of the invention.

In a preferred aspect, the process of manufacture of the orally deliverable tablet comprising at least one biologically active compound selected from proteins/peptides, their conjugates, and/or cation-polypeptide conjugate complexes possessing resistance to enzymatic degradation comprising the steps:
1. Grinding a suitable saturated or unsaturated C4-C12 fatty acid and/or salts of such a fatty acid.
2. Granulating the resulting fatty acid obtained from step (1) with an organic solvent.
3. Air-drying the granules obtained from step (2).
4. Rasping the dried granules through a mesh to obtain granules of desired particle size
5. Blending the fatty acid granules with the cation-insulin compound conjugate, disintegrant, binder and other excipients.
6. Tablet compression, polishing and packing In yet another preferred aspect, the process of manufacture of the orally deliverable tablet comprising at least one biologically active compound selected from proteins/peptides, their conjugates, and/or cation-polypeptide conjugate complexes possessing resistance to enzymatic degradation comprising the steps:
1. Grinding suitable saturated or unsaturated C4-C12 fatty acid and/or salts of such a fatty acid such as sodium caprate, PVP-K-30.
2. Suspending IN-105 in an organic solvent using PVPK-30 as a binder to form a wet mass
3. Granulation of the resulting components using PVP-K30 as a binder
4. Rasping of dried Sodium caprate granules through 45# (355 µm)
5. Blending of sodium caprate granules with other excipients.
6. Tablet compression, polishing and packing.

According to the most significant aspects of the invention the term "stable" as it applies to the composition of the present invention is meant for purposes of the invention to mean that the formulation remains undegraded or does not degrade to an unacceptable extent even after exposure of the formulation to a range of storage conditions selected from the group comprising (i) temperature of about 2-8° C., 25° C., 30° C. and 40° C. (ii) 25° C./60% relative humidity (RH), 30° C./65% relative humidity, 40° C./75% relative humidity for at least one year or any combination of the illustrated conditions. In context of the nature of the present invention undegraded or does not degrade to an unacceptable extent shall mean that the dosage components remain well within the applicable limits of stability during the test periods.

According to one aspect of the invention testing for stability is conducted for a period of 1-12 months, preferably 1 month, preferably 2 months, preferably 3 months, preferably 4 months, preferably 5 months, preferably 6 months, preferably 7 months, preferably 9 months, preferably 11 months and most preferably 12 months. The invention contemplates the stability attributes of the dosage form to remain compatible for a period extending to about 2 years.

The stability attributes of pharmaceutical composition of the instant invention is evaluated at different test conditions of temperature such as lower temperature conditions in the range of 2-8° C., ambient room temperature conditions of 25° C.-30° C. and slightly elevated temperature conditions of 40° C. As may be apparent to one skilled in the art, the temperature conditions and, the stabilities established in the said temperature conditions may not be strictly limited to the temperature conditions tested herein. The invention contemplates the extension of the stability attributes displayed during the test conditions to be established within the scope of a broad range of lower and elevated temperatures. The composition and its stability attributes are not subjected to much variation at temperatures ranging from 2-40° C.

The stability attributes of pharmaceutical composition of the instant invention is evaluated at different test conditions of relative humidity such as RH conditions 25° C./60% relative humidity (RH), 30° C./65% relative humidity, 40° C./75% relative humidity or combination of the conditions illustrated herein. As may be apparent to one skilled in the art, the relative humidity conditions and the stabilities established in the said temperature conditions may not be strictly limited to the relative humidity conditions tested herein. The invention contemplates the extension of the stability attributes displayed during the test conditions to be established within the scope of a broad range of relative humidity temperatures not explicitly disclosed herein. The composition and its stability attributes are not subjected to much variation at relative humidities ranging from 25° C./60%-40° C./75%.

According to one aspect of the invention the composition of the instant invention is characterized in that at least 95%±2% of the composition remains undegraded over exposure to conditions selected from the group comprising.
  (a) temperature range of about 2-8° C. or 25° C.-40° C.
  (b) 25° C./60% relative humidity (RH), 30° C./65% relative humidity, 40° C./75% relative humidity for over a period of at least 6 months.

According to one aspect of the invention the composition of the instant invention is characterized in that at least 95%±2% of the composition remains undegraded over exposure to conditions selected from the group comprising
  (a) temperature range of about 2-8° C. or 25° C.-40° C.
  (b) 25° C./60% relative humidity (RH), 30° C./65% relative humidity, 40° C./75% relative humidity for over a period of at least 6 months.

According to yet another aspect of the instant invention the various stability attributes tested for the tablet composition include but is not limited to hardness, disintegration time dissolution profile and the chromatographic purity.

Accordingly, as per various embodiments of the invention exhibits various advantages with respect to the dosing and convenient method of administration. The invention constitutes yet another advantage over the prior art compositions as the inventors propose that the claimed rationally designed oral formulation of IN-105 with measured components of other excipients and the process of manufacturing the orally administrable tablets are easily scalable without affecting the release profile in-vitro or in-vivo. Further, attributed to this rationally designed oral formulation and the process of making the same, the scalability factor does not impact the in-vivo drug performance or its in-vivo release profile.

One of the important aspects of the invention relates to spray drying the composition to obtain an homogenous, amorphous mixture of the cation-insulin conjugate complex.

A variety of parameters may be optimized to modify the average size of the droplets. Droplet size can be influenced, e.g., by adjusting the near supercritical fluid pressure or pressure of the high-pressure gas, adjusting the suspension or solution pressure, adjusting the flow rate of the suspension or solution, choice of the nozzle conduit internal diameter, adjusting the temperature of the drying gas, adjusting the pressure inside the particle formation vessel, changing the concentrations of suspension or solution constituents, and/or the like. For example, the suspension or solution can be supplied to the mixing chamber at from about 0.5 ml/min to about 40 ml/min to spray from a 100 μm internal diameter nozzle orifice; lower rates forming smaller droplets and faster rates forming larger droplets. In the methods, formation of droplets ranging in mass median diameter from about 1 μm to about 200 μm is preferred.

In the present invention, the temperature at which spray-drying is efficiently conducted is normally in the range between about 80° C. and about 300° C., preferably between about 100° C. and about 180° C. Temperature control may be particularly important for maintaining the stability of product particles which are formed or contain highly temperature sensitive substances.

The pharmaceutical compositions obtained using certain embodiments of the invention can be administered to any animal that can experience the beneficial effects of the compounds of the invention. Foremost among such animals are humans, although the invention is not intended to be so limited.

The method of preparing powdered formulation particles in the invention can comprise, for example, preparing an aqueous suspension or solution of a bioactive material and a polyol optionally with one or more of other compatible pharmaceutical excipients, forming a mixture of the solution or suspension with a pressurized gas, spraying ultrafine droplets by depressurizing the mixture, and drying the droplets into powder particles by exchanging the spray gases with drying gases, e.g., to by spraying into a drying chamber of the spray dry apparatus.

The term "solvent" refers to the liquid in which the material forming the bulk of the spray dried particle is dissolved, suspended, or emulsified for delivery to the atomizer of a spray dryer and which is evaporated into the drying gas, whether or not the liquid is a solvent or non-solvent for the material. The choice of solvent depends on the bulk material and the form of the material fed to the atomizer, e.g., whether the material is to be dissolved, suspended, or emulsified in the solvent. The most preferred solvent in context of the present invention is water.

When employing spray-drying method, a raw material in the form of a solution comprising at least one of active ingredients selected from the group consisting of cation-insulin compound conjugate in combination with the diluents is spray-dried to produce particles.

The size of the particles of drug solution is a function of the atomizer used to spray the polymer solution, the atomizer pressure, the flow rate, the ingredients used, their concentration, the type of solvent, the viscosity, the temperature of spraying (both inlet and outlet temperature), and the molecular weight of the therapeutic agent. Generally, the higher the molecular weight, the larger the particle size, assuming the concentration is the same.

One of the aspects of the present invention relates to a comparative dog clamp study of two prototype formulations of cation-insulin compound conjugates oral compositions prepared by direct compression method and the spray drying method.

The following measurements were performed: glucose infusion rate, plasma insulin concentration, and plasma glucose levels (to allow an estimation of endogenous insulin compound release). The glucose infusion rate required to maintain euglycemia provides an index of insulin compound action. The glucose infusion rates and plasma insulin levels were evaluated and compared.

The prototype formulations prepared by the spray dried method show consistent levels of drug absorption and resultant glucose infusion rate without loss of stability or biological activity.

The prototype formulation I (Formulation 862) has the following composition

| Ingredient | Quantity (mg) per tablet |
|---|---|
| IN-105 | 6 |
| Sodium caprate | 150 |
| Mannitol | 150 |
| Explotab (Croscarmellose sodim) | 25 |

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The invention will be better understood from the following Examples. However, those of ordinary skill in the art will readily understand that these Examples are merely illustrative of the invention that is defined in the claims that follow thereafter. The following Examples represent preferred embodiments of the present invention.

Example I

Drug formulations in accordance with the present invention were prepared and tested. Accordingly, required amount of ground Sodium caprate was weighed accurately in to a planetary mixture and the granulate with 700 ml of isopropyl alcohol. The amount of isopropyl alcohol added to convert the powder mixture to granular form was calculated. The wet mass was scraped every 5 minutes, such that the mixture does not stick to the wall of the planetary mixture. The wet mass was passed through 18# sieve in a wet granulator and air dried overnight under the hood.

Moisture Content of Granules: Sample Weight=0.662 gm; % of moisture content=2.27%

Appropriate quantity of IN-105, sodium caprate granules, Kollidon CL and pearlitol was weighed and passed through a 60# sieve and mixed in a double cone blender for 20 minutes at a speed of 12 r.p.m. After homogenous mixing for 20 minutes, the blend was lubricated with aerosol and magnesium stearate for 3 minutes at a speed of 88-90 r.p.m.

TABLE I

| INGREDIENTS | PER TABLET (MG) | FOR 1000 gm |
|---|---|---|
| IN-105* | 5.8207 | 17.27 |
| Sodium Caprate granules | 150.000 | 445.10 |
| Kollidon CL | 33.700 | 100.00 |
| Pearlitol SD 200 | 144.1093 | 427.62 |
| Aerosil 200 Pharma | 1.685 | 5.00 |
| Magnesium Stearate | 1.685 | 5.00 |
| | Total -337 mg | Total-1000 gm |

The tablets prepared as per the example I, were tested in 26 hrs fasted six healthy male beagle dogs. Each tablet was administered with 20 ml of water. The blood samples were collected for measuring blood glucose and plasma insulin levels. As represented in FIG. 1 and FIG. 2 the tablet resulted in a rapid increase of plasma insulin levels showing a Cmax of about 100 mU/ml with a Tmax of 20 minutes from the time of administration resulting in a corresponding drop of about 35% in plasma glucose concentration.

The tablets thus produced were subjected to stability studies as per the ICH guidelines. The long term studies were carried out at 2-8 deg C. and 25 deg C. while the accelerated stability was carried out at 30 deg C./65% RH and 40 deg C./75% RH.

Stability of 5 mg IN-105 tablets at 2-8 deg C.

| Testing Intervals In months | Hardness NMT 5.0 Kg/cm2 | Disintegration time NMT 15 min | HMWP NMT 3.0% | Chromatographic purity NLT 93% | Assay (in mg) | % Assay (w.r.t Label Claim) | Disssolution NLT 75.0% at 15 minutes |
|---|---|---|---|---|---|---|---|
| 0 | 1.58 | 1.49 | 0.053 | 95.3 | 5.08 | 102% | 99.1% |
| 1 | 1.58 | 1.50 | 0.052 | 94.8 | 5.07 | 101% | 92.6% |
| 3 | 1.51 | 1.50 | 0.059 | 94.5 | 5.07 | 101% | 104.9% |
| 6 | 1.42 | 1.44 | 0.065 | 94.5 | 5.14 | 103% | 103.7% |
| 9 | 1.38 | 1.41 | 0.056 | 94.7 | 5.1 | 102% | 99.3% |
| 12 | 1.40 | 1.45 | 0.060 | 94.4 | 5.08 | 102% | 95.6% |

Stability of 5 mg IN-105 tablets at 25 deg C. 60% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay (w.r.t Label Claim) | Disssolution NLT 75.0% at 15 minutes |
|---|---|---|---|---|---|---|---|
| 0 | 1.58 | 1.49 | 0.053 | 95.3 | 5.08 | 102.0 | 99.1 |
| 1 | 1.70 | 1.40 | 0.13 | 94.8 | 5.06 | 101.0 | 77.2 |
| 2 | 1.63 | 1.38 | 0.26 | 94.0 | 5.04 | 101.0 | 85.6 |
| 3 | 1.66 | 1.36 | 0.23 | 94.5 | 5.09 | 102.0 | 95.9 |
| 6 | 1.84 | 1.34 | 0.19 | 94.7 | 4.71 | 94.0 | 84.7 |
| 9 | 1.59 | 1.33 | 0.19 | 94.0 | 4.69 | 94.0 | 85.2 |
| 12 | 1.74 | 1.38 | 0.25 | 94.3 | 4.85 | 97.0 | 85.6 |

Stability of 5 mg IN-105 tablets at 30 deg C. 65% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay (w.r.t Label Claim) | Disssolution NLT 75.0% at 15 minutes |
|---|---|---|---|---|---|---|---|
| 0 | 1.58 | 1.49 | 0.053 | 95.3 | 5.08 | 102.0 | 99.1 |
| 1 | 1.69 | 1.48 | 0.06 | 95.2 | 5.10 | 102.0 | 84.1 |
| 2 | 1.55 | 1.50 | 0.059 | 94.8 | 5.12 | 102.0 | 82.6 |
| 3 | 1.55 | 1.50 | 0.070 | 94.6 | 5.13 | 102.0 | 100.4 |
| 6 | 1.63 | 1.44 | 0.130 | 94.3 | 4.92 | 98.0 | 94.3 |

Stability of 5 mg IN-105 tablets at 40 deg C. 70% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay (w.r.t Label Claim) | Disssolution NLT 75.0% at 15 minutes |
|---|---|---|---|---|---|---|---|
| 0 | 1.58 | 1.49 | 0.053 | 95.3 | 5.08 | 102.0 | 99.1 |
| 1 | 1.58 | 1.43 | 0.110 | 94.2 | 4.84 | 97.0 | 86.0 |
| 2 | 1.54 | 1.45 | 0.130 | 93.8 | 4.79 | 96.0 | 90.0 |
| 3 | 1.51 | 1.48 | 0.150 | 93.9 | 4.64 | 93.0 | 79.0 |
| 6 | 1.42 | 1.53 | 0.200 | 93.3 | 4.75 | 96.0 | 78.0 |

Example 2

Milled sodium caprate was accurately weighed and taken in a planetary mixer and mixed for 2 minutes. Required quantities of IN-105 weighed was added to isopropanol with 0.35% w/w of polyvinylpyrrolidone to form a suspension and stirred well for 30 minutes using a magnetic stirrer. Appropriate amounts of isopropanol was added during granulation.

The granules were mixed for 15 min in planetary mixer and passed through 14# sieve a dried in Hot Air Oven for 2 hrs at 30° C.

TABLE 2

| INGREDIENTS | QUANTITY (per tablet) | QUANTITY (G) |
|---|---|---|
| Sodium Caprate | 150 mg | 192.67 |
| IN-105 | 5.7078 mg | 7.33 |
| PVP-K 30 | 5.45 mg | 7.00 |

Speed of Planetary mixer=4 for 15 min. Volume of IPA added=200 ml.

0.7 gm (0.35%) PVP+7.33 GM. IN-105 was suspended in 80 ml of IPA. Remaining 6.3 gm of PVP was suspended in 40 ml of IPA. Remaining amount of IPA was added to form a hard wet mass.

Blending Process:

Accurately weighed quantity of IN-105+Sodium caprate+PVP K-30 granules, Pearlitol and Kollidon CL were passed through 45# sieve and mixed in a octagonal blender. After homogenous mixing the blend was lubricated with Aerosil and Magnesium stearate, mixed well and compressed into tablets.

TABLE 3

| INGREDIENTS | PER TABLET (MG) | FOR 50 gm (G) |
|---|---|---|
| IN-105 | 5.7078 | 0.92 |
| Sodium Caprate granules | 150.00 | 24.19 |
| PVP K-30 | 5.45 | 0.88 |
| Pearlitol | 114.742 | 18.51 |
| Kollidon CL | 31 | 5.00 |
| Aerosil 200 Pharma | 1.55 | 0.25 |
| Magnesium Stearate | 1.55 | 0.25 |
| | Total-310 mg | Total-50 g |

Tablets prepared as per the example 2, were tested in 26 hours fasted six healthy male beagle dogs. Each tablet was administered with 20 ml of water. The blood samples were collected for measuring blood glucose and plasma insulin levels. As represented in FIG. 3 and FIG. 4, the tablets resulted in a rapid increase in plasma insulin levels showing a Cmax of about 75 mU/ml with a Tmax of 20 minutes from the time of administration. This resulted in a corresponding drop of about 35% in plasma glucose concentration from the baseline.

The tablets thus produced were subjected to stability studies as per the ICH guidelines. The long term studies were carried out at 2-8 deg C. and 25 deg C. while the accelerated stability was carried out at 30 deg C./65% RH and 40 deg C./75% RH.

Stability of 5 mg IN-105 tablets at 2-8 deg C.

| Testing Intervals In months | Hardness NMT 5.0 Kg/cm2 | Disintegration time NMT 15 min | HMWP NMT 3.0% | Chromatographic purity NLT 93% | Assay (in mg) | % Assay (w.r.t Label Claim) | Disssolution NLT 75.0% at 15 minutes |
|---|---|---|---|---|---|---|---|
| 0 | 1.88 | 2.10 | 0.13 | 95.3 | 5.34 | 107.0 | 94.0% |
| 1 | 1.58 | 1.50 | 0.052 | 94.8 | 5.07 | 102.0 | 90.0% |
| 3 | 1.51 | 1.50 | 0.059 | 94.5 | 5.07 | 102.0 | 102.0% |
| 6 | 1.42 | 1.44 | 0.065 | 94.5 | 5.14 | 103.0 | 86.0 |
| 9 | 1.38 | 1.41 | 0.056 | 94.7 | 5.21 | 104.0 | 95.0 |
| 12 | 1.40 | 1.45 | 0.060 | 94.4 | 5.18 | 104.0 | 89.0 |

Stability of 5 mg IN-105 tablets at 25 deg C. 60% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t Label Claim | Dissolution NLT 75.0% at 15 minutes |
|---|---|---|---|---|---|---|---|
| 0 | 1.88 | 2.1 | 0.13 | 95.3 | 5.34 | 107.0 | 94.0% |
| 1 | 1.60 | 1.40 | 0.13 | 94.8 | 5.26 | 105.0 | 89.0 |
| 2 | 1.60 | 1.38 | 0.26 | 94.0 | 5.22 | 105.0 | 91.0 |
| 3 | 1.52 | 1.36 | 0.23 | 94.5 | 5.29 | 106.0 | 94.0 |
| 6 | 1.48 | 1.34 | 0.19 | 94.7 | 5.17 | 103.0 | 90.0 |
| 9 | 1.45 | 1.33 | 0.19 | 94.0 | 5.13 | 103.0 | 103.0 |
| 12 | 1.48 | 1.38 | 0.25 | 94.3 | 5.20 | 104.0 | 87.0 |

Stability of 5 mg IN-105 tablets at 30 deg C. 65% RH.

| Testing Intervals In months | Hardness NMT 5.0 Kg/cm2 | Disintegration time NMT 15 min | HMWP NMT 3.0% | Chromatographic purity NLT 93% | Assay (im mg) | % Assay w.r.t Label Claim | Dissolution NLT 75.0% at 15 minutes |
|---|---|---|---|---|---|---|---|
| 0 | 1.88 | 2.1 | 0.13 | 95.3 | 5.34 | 107.0 | 94.0% |
| 1 | 1.61 | 1.48 | 0.06 | 95.2 | 4.97 | 99.0 | 90.0% |
| 2 | 1.58 | 1.50 | 0.059 | 94.8 | 4.92 | 98.0 | 102.0% |
| 3 | 1.51 | 1.50 | 0.070 | 94.6 | 4.88 | 98.0 | 86.0% |
| 6 | 1.42 | 1.44 | 0.130 | 94.3 | 4.79 | 96.0 | 79.0% |

Stability of 5 mg IN-105 tablets at 40 deg C. 75% RH.

| Testing Intervals In months | Hardness NMT 5.0 Kg/cm2 | Disintegration time NMT 15 min | HMWP NMT 3.0% | Chromatographic purity NLT 90% | Assay (im mg) | % Assay w.r.t Label Claim | Dissolution NLT 75.0% at 15 minutes |
|---|---|---|---|---|---|---|---|
| 0 | 1.88 | 2.1 | 0.13 | 95.3 | 5.34 | 107.0 | 94.0% |
| 1 | 1.58 | 2.0 | 0.17 | 94.2 | 5.09 | 102.0 | 96.0% |
| 2 | 1.54 | 2.3 | 0.19 | 93.7 | 5.06 | 101.0 | 84.0% |
| 3 | 1.51 | 2.2 | 0.16 | 93.9 | 5.01 | 100.0 | 89.0% |
| 6 | 1.42 | 1.9 | 0.29 | 93.3 | 4.91 | 98.0 | 92.0% |

Example 3

Accurately weighed Qty of IN-105, Sodium caprate+Beta-Cyclodextrin complex, Sodium bicarbonate and Kollidon CL were passed through 45# sieve and mixed in a Polyethylene bag. After homogenous mixing the blend was lubricated with Aerosil and Magnesium stearate, mixed well and compressed into tablets.

TABLE 4

| INGREDIENTS | PER TABLET (MG) | FOR 50 gm (G) |
|---|---|---|
| IN-105 | 5.7078 | 1.30 |
| Beta-Cyclodextrin | 40.38 | 9.18 |
| Sodium Caprate granules | 75.00 | 17.05 |
| Sodium bicarbonate | 74.71 | 16.98 |
| Kollidon CL | 22 | 5.00 |

TABLE 4-continued

| INGREDIENTS | PER TABLET (MG) | FOR 50 gm (G) |
|---|---|---|
| Aerosil 200 Pharma | 1.1 | 0.25 |
| Magnesium Stearate | 1.1 | 0.25 |
| | Total-220 mg | Total-50 g |

Stability of 5 mg IN-105 tablets at 2-8 deg C.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0  | 1.58 | 1.49 | 0.053 | 95.3 | 4.99 | 99.0  | 95.0% |
| 1  | 1.58 | 1.50 | 0.052 | 94.8 | 4.99 | 99.0  | 91.0% |
| 3  | 1.51 | 1.50 | 0.059 | 94.5 | 5.01 | 100.0 | 85.0% |
| 6  | 1.42 | 1.44 | 0.065 | 94.5 | 4.96 | 99.0  | 101.0% |
| 9  | 1.38 | 1.41 | 0.056 | 94.7 | 4.93 | 99.0  | 92.0% |
| 12 | 1.40 | 1.45 | 0.060 | 94.4 | 4.97 | 99.0  | 89.0% |

Stability of 5 mg IN-105 tablets at 25 deg C. 60% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0  | 1.58 | 1.49 | 0.053 | 95.3 | 4.99 | 99.0  | 95.0% |
| 1  | 1.60 | 1.40 | 0.13  | 94.8 | 5.06 | 101.0 | 89.0% |
| 2  | 1.60 | 1.38 | 0.26  | 94.0 | 4.93 | 99.0  | 91.0  |
| 3  | 1.52 | 1.36 | 0.23  | 94.5 | 4.92 | 98.0  | 101.0 |
| 6  | 1.48 | 1.34 | 0.19  | 94.7 | 4.95 | 99.0  | 87.0  |
| 9  | 1.45 | 1.33 | 0.19  | 94.0 | 4.91 | 98.0  | 90.0  |
| 12 | 1.48 | 1.38 | 0.25  | 94.3 | 4.87 | 97.0  | 85.0  |

Stability of 5 mg IN-105 tablets at 30 deg C. 65% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.58 | 1.49 | 0.053 | 95.3 | 4.99 | 99.0  | 95.0% |
| 1 | 1.61 | 1.48 | 0.06  | 95.2 | 5.00 | 100.0 | 94.0% |
| 2 | 1.58 | 1.50 | 0.059 | 94.8 | 4.81 | 96.0  | 92.0% |
| 3 | 1.51 | 1.50 | 0.070 | 94.6 | 4.83 | 96.0  | 84.0% |
| 6 | 1.42 | 1.44 | 0.130 | 94.3 | 4.72 | 94.0  | 90.0% |

Stability of 5 mg IN-105 tablets at 40 deg C. 75% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.58 | 1.49 | 0.053 | 95.3 | 4.99 | 99.0 | 95.0% |
| 1 | 1.58 | 1.50 | 0.110 | 94.2 | 4.88 | 98.0 | 90.0  |
| 2 | 1.57 | 1.48 | 0.130 | 93.6 | 4.92 | 94.0 | 81.0  |
| 3 | 1.51 | 1.50 | 0.150 | 93.9 | 4.77 | 95.0 | 79.0  |
| 6 | 1.42 | 1.44 | 0.200 | 93.3 | 4.64 | 92.8 | 76.0  |

Example 4

Accurately weighed Qty of IN-105, Sodium Lauryl sulphate, Kollidon CL and Pearlitol were passed through 45# sieve and mixed in a octagonal blender. After homogenous mixing, the blend was lubricated with Aerosil and Magnesium stearate, mixed well and compressed in to Tablets.

TABLE 5

| INGREDIENTS | PER TABLET (MG) | FOR 50 gm (G) |
|---|---|---|
| IN-105 60# | 5.7078 | 1.90 |
| Sodium Lauryl sulfate | 50.0 | 16.67 |
| Kollidon CL | 15.00 | 5.00 |
| Pearlitol SD 200 | 77.7922 | 25.93 |
| Aerosil 200 Pharma | 0.75 | 0.25 |
| Magnesium Stearate | 0.75 | 0.25 |
| | Total-150 mg | Total-50 g |

Tablets prepared as described in example 4, were tested in 26 hrs fasted six healthy male beagle dogs. Each tablet was administered with 20 ml of water. The blood samples were collected for measuring blood glucose and plasma insulin levels. Results obtained is represented in FIG. 5 and FIG. 6. The tablets thus produced were subjected to stability studies as per the ICH guidelines. The long term studies were carried out at 2-8 deg C. and 25 deg C. while the accelerated stability was carried out at 30 deg C./65% RH and 40 deg C./75% RH.

Stability of 5 mg IN-105 tablets at 2-8 deg C.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.64 | 1.62 | 0.064 | 95.7 | 5.16 | 103.2 | 97.6% |
| 1 | 1.61 | 1.58 | 0.068 | 95.2 | 5.24 | 104.8 | 98.4% |
| 2 | 1.62 | 1.56 | 0.072 | 95.5 | 5.20 | 104.0 | 97.2% |
| 3 | 1.59 | 1.49 | 0.070 | 95.3 | 5.01 | 100.0 | 95.0% |
| 6 | 1.59 | 1.54 | 0.076 | 94.8 | 4.94 | 98.8 | 92.7% |
| 9 | 1.55 | 1.42 | 0.082 | 94.2 | 5.10 | 102.0 | 88.4% |
| 12 | 1.50 | 1.46 | 0.090 | 94.1 | 4.91 | 98..2 | 90.0% |

Stability of 5 mg IN-105 tablets at 25 deg C. 60% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.64 | 1.62 | 0.064 | 95.7 | 5.16 | 103.2 | 97.6% |
| 1 | 1.62 | 1.66 | 0.070 | 95.1 | 5.26 | 105.2 | 90.0% |
| 2 | 1.60 | 1.54 | 0.074 | 95.0 | 5.14 | 102.8 | 94.1% |
| 3 | 1.64 | 1.59 | 0.072 | 95.2 | 4.97 | 99.6 | 89.1% |
| 6 | 1.57 | 1.56 | 0.081 | 94.6 | 4.82 | 96.4 | 92.0% |
| 9 | 1.49 | 1.42 | 0.086 | 94.1 | 4.98 | 99.6 | 96.0% |
| 12 | 1.44 | 1.47 | 0.092 | 93.7 | 4.87 | 97.4 | 98.4% |

Stability of 5 mg IN-105 tablets at 30 deg C. 65% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.64 | 1.62 | 0.064 | 95.7 | 5.16 | 103.2 | 97.6% |
| 1 | 1.62 | 1.62 | 0.072 | 95.3 | 5.10 | 102.0 | 98.6% |
| 2 | 1.62 | 1.60 | 0.076 | 94.8 | 5.01 | 100.2 | 92.4% |
| 3 | 1.50 | 1.46 | 0.082 | 94.4 | 4.84 | 96.8 | 94.0% |
| 6 | 1.44 | 1.29 | 0.094 | 93.6 | 4.79 | 95.8 | 88.4% |

Stability of 5 mg IN-105 tablets at 40 deg C. 70% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 0 | 1.64 | 1.62 | 0.064 | 95.7 | 5.16 | 103.2 | 97.6% |
| 1 | 1.58 | 1.59 | 0.072 | 95.1 | 5.08 | 102.0 | 92.0% |
| 2 | 1.52 | 1.54 | 0.079 | 94.5 | 4.92 | 98.4 | 94.5% |

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t. Label Claim | Dissolution NLT 75.0% at 15 minutes |
|---|---|---|---|---|---|---|---|
| 3 | 1.42 | 1.48 | 0.086 | 94.0 | 4.86 | 97.2 | 89.7% |
| 6 | 1.38 | 1.46 | 0.102 | 93.2 | 4.64 | 92.8% | 90.1% |

Example 5

Preparation of Sodium Caprate, Sodium Bicarbonate and Pearlitol Granules with PVP K-30 (2% W/W) as Binder and PEG 6000 (1% W/W) as Plasticizer and IN-105 Added During Granulation Accurately weighed quantity of Ground Sodium caprate, Sodium bicarbonate and Pearlitol was taken in planetary mixer, dry mixing was done for 5 min. Meanwhile PVP K 30 was dissolved in IPA and IN-105 was suspended. PEG 6000 was dissolved in water (5% v/v). The Solution were stirred well using Magnetic Stirrer. Sodium caprate, Sodium bicarbonate and Pearlitol were granulated using PVPK and PEG solution as granulating agent. The process was carried out for 20 min. The Wet mass formed was passed through 18# sieve in Wet granulator and dried in LAF.

Volume of IPA Added—130 ml.

100 ml=IN-105+PVP k. 6 ml=PEG in water. Speed of Planetary mixer=2-4 for 20 min.

Speed of Wet granulator—200 rpm.

Moisture Content of Granules.

Weight of Sample—0.525 gm.

% Moisture content—1.99%.

TABLE 6

| Ingredients | Quantity per Tablet (mg) | For 250 gm batch |
|---|---|---|
| IN-105 | 10.6952 | 8.60 |
| Sodium caprate | 150 | 120.55 |
| Sodium bicarbonate | 90 | 72.33 |
| Pearlitol 200 SD | 60.37 | 48.52 |
| PVP k-30 (2% w/w) | 6.22 | 5 |
| PEG 6000 (1% w/w) | 3.11 | 2.5 |

TABLE 7

| INGREDIENTS | PER TABLET (MG) | FOR 200 gm (G) |
|---|---|---|
| IN-105 | 10.6952 | 5.94 |
| Sodium Caprate | 150.00 | 83.33 |
| Sodium Bicarbonate | 90.00 | 50.00 |
| Pearlitol 200 SD | 60.37 | 33.54 |
| PVP K 30 | 6.22 | 3.46 |
| PEG 6000 | 3.11 | 1.73 |
| Kollidon CL | 36.00 | 20.00 |
| Aerosil 200 Pharma | 1.8 | 1.00 |
| Magnesium Stearate | 1.8 | 1.00 |
| | Total-360 mg | Total-200 gm |

Accurately weighed quantity of IN-105+Sodium caprate+Sodium bicarbonate+Pearlitol+PVP K 30 and PEG granules were passed through 35# sieve and mixed with Kollidon CL in a double cone blender. After homogenous mixing the blend was lubricated with Aerosil and Magnesium stearate, mixed well and compressed into tablets.

The tablets thus produced were subjected to stability studies as per the ICH guidelines. The long term studies were carried out at 2-8 deg C. and 25 deg C. while the accelerated stability was carried out at 30 deg C./65% RH and 40 deg C./75% RH.

Stability of 5 mg IN-105 tablets at 2-8 deg C.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t Label Claim | Dissolution NLT 75.0% at 15 minutes |
|---|---|---|---|---|---|---|---|
| 0 | 1.58 | 1.49 | 0.053 | 95.3 | 5.08 | 102.0 | 96.0% |
| 1 | 1.58 | 1.50 | 0.052 | 94.8 | 5.07 | 102.0 | 92.0% |
| 3 | 1.51 | 1.50 | 0.059 | 94.5 | 5.07 | 102.0 | 86.7% |
| 6 | 1.42 | 1.44 | 0.065 | 94.5 | 5.14 | 103.0 | 90.3% |
| 9 | 1.38 | 1.41 | 0.056 | 94.7 | 5.1 | 103.0 | 98.0% |
| 12 | 1.40 | 1.45 | 0.060 | 94.4 | 5.08 | 102.0 | 89.2% |

Stability of 5 mg IN-105 tablets at 25 deg C. 60% RH.

| Testing Intervals In months | Hardness NMT 5.0 Kg/cm2 | Disintegration time NMT 15 min | HMWP NMT 3.0% | Chromatographic purity NLT 93% | Assay (in mg) | % Assay w.r.t Label Claim | Dissolution NLT 75.0% at 15 minutes |
|---|---|---|---|---|---|---|---|
| 0 | 1.58 | 1.49 | 0.053 | 95.3 | 5.08 | 102.0 | 96.0% |
| 1 | 1.60 | 1.40 | 0.13 | 94.8 | 5.06 | 102.0 | 102.0% |
| 2 | 1.60 | 1.38 | 0.26 | 94.0 | 5.04 | 101.0 | 93.1% |
| 3 | 1.52 | 1.36 | 0.23 | 94.5 | 5.09 | 102.0 | 91.2% |
| 6 | 1.48 | 1.34 | 0.19 | 94.7 | 4.71 | 94.0 | 84.6% |
| 9 | 1.45 | 1.33 | 0.19 | 94.0 | 4.69 | 94.0 | 81.9% |

Stability of 5 mg IN-105 tablets at 30 deg C. 65% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t Label Claim | Dissolution NLT 75.0% at 15 minutes |
|---|---|---|---|---|---|---|---|
| 0 | 1.58 | 1.49 | 0.053 | 95.3 | 5.08 | 102.0 | 96.0% |
| 1 | 1.61 | 1.48 | 0.06 | 95.2 | 5.10 | 104.0 | 89.2% |
| 2 | 1.54 | 1.52 | 0.070 | 94.4 | 5.08 | 104.0 | 92.0% |
| 3 | 1.51 | 1.50 | 0.070 | 94.6 | 5.13 | 104.0 | 89.0% |
| 6 | 1.42 | 1.44 | 0.130 | 94.3 | 4.71 | 94.2 | 84.7% |

Stability of 5 mg IN-105 tablets at 40 deg C. 75% RH.

| Testing Interval In months | Hardness NMT 5.0 Kg/cm2 | Disintegration time NMT 15 min | HMWP NMT 3.0% | Chromatographic purity NLT 93% | Assay (in mg) | % Assay w.r.t Label Claim | Dissolution NLT 75.0% at 15 minutes |
|---|---|---|---|---|---|---|---|
| 0 | 1.58 | 1.49 | 0.053 | 95.3 | 5.08 | 102.0 | 96.0% |
| 1 | 1.58 | 1.50 | 0.110 | 94.2 | 4.84 | 97.0 | 98.0% |
| 2 | 1.50 | 1.48 | 0.12 | 93.6 | 4.78 | 96.0 | 87.6% |
| 3 | 1.51 | 1.50 | 0.150 | 93.9 | 4.64 | 88.0 | 84.7% |
| 6 | 1.42 | 1.44 | 0.200 | 93.3 | 4.75 | 96.0 | 80.0% |

These are preferred dose proportional formulations giving desirable drug release profiles. These formulations provide an approximately consistent release of IN-105 have been envisioned.

Example 6

1.663 gm of IN-105 and 50 g of sodium caprate were dissolved in water by adjusting the pH to 8.28 using 10% sodium hydroxide. Solution was take for spray drying. The solution was spray dried at 80° C. in a cocurrent fashion. Atomization pressure used was 1.5 kg/cm2, and the feed flow rate to the spray drier was 2 ml/min. The purity of the spray dried sample was ~98% and from total expected 52 gm, a total of 16 gm granules and 1.5 gm fine powder was recovered.

This spray dried powder was mixed with other formulation excipients like mannitol, explotab, colloidal silica and magnesium stearate and compressed in to tablet form. These tablets were then tested in dog clamp model to see the pharmacokinetic and pharmacodynamic response.

Example 7

A feed slurry of IN105 having concentration 35 g/l was used for obtaining spray dried samples. Excipients used were Mannitol and Sodium caprate. To a mixture of 1050 mg Sodium caprate and 1015 mg Mannitol, 20 ml of solution containing 1 ml of feed slurry was added and mixed thoroughly. The solution was spray dried at 80° C. in a cocurrent fashion. Atomization pressure used was 1.5 kg/cm2, and the feed flow rate to the spray drier was 2 ml/min. A recovery of around 60% was obtained for the sample and its purity of the spray dried sample was ~98%.

Example 8

A feed slurry of IN105 having concentration 35 g/l was used for obtaining spray dried samples. Excipients used were Mannitol and Sodium caprate. To a mixture of 1050 mg Sodium Caprate and 945 mg of Mannitol, 20 ml of solution containing 3 ml of feed slurry was added and mixed thoroughly. The solution was spray dried at 80° C. in a cocurrent fashion. Atomization pressure used was 1.2 kg/cm2, and the feed flow rate to the spray drier was 2 ml/min. A recovery of around 60% was obtained for the sample and its purity was later found out to be 98.6%.

Example 9

A feed slurry of IN105 having concentration 35 g/l was used for obtaining spray dried samples. Excipients used were Mannitol and Sodium caprate. To a mixture of 1050 mg Sodium caprate and 1015 mg Mannitol, 20 ml of solution containing 1 ml of feed slurry was added and mixed thoroughly. The solution was spray dried at 120° C. in a cocurrent fashion. Atomization pressure used was 1.5 kg/cm2, and the feed flow rate to the spray drier was 2 ml/min. A recovery of around 60% was obtained for the sample and its purity was later found out to be 99.5%.

Example 10

A feed slurry of IN105 having concentration 35 g/l was used for obtaining spray dried samples. Excipients used were Mannitol and Sodium caprate. To a mixture of 1050 mg Sodium Caprate and 945 mg of Mannitol, 20 ml of solution containing 3 ml of feed slurry was added and mixed thoroughly. The solution was spray dried at 120° C. in a cocurrent fashion. Atomization pressure used was 1.2 kg/cm2, and the feed flow rate to the spray drier was 2 ml/min. A recovery of around 60% was obtained for the sample and its purity was later found out to be 98.3%.

Example 11

A feed slurry of IN105 having concentration 11.5 g/l was used for obtaining spray dried samples. Excipients used were Mannitol and Sodium caprate. To a mixture of 3000 mg Sodium Caprate and 2885 mg of Mannitol, 50 ml of solution containing 10 ml of feed slurry was added and mixed thoroughly. The solution was spray dried at 150° C. in a countercurrent fashion. Atomization pressure used was 0.86 kg/cm2, and the feed flow rate to the spray drier was 4 ml/min. The sample purity was found out to be 94.71%.

The two prototype formulations [Formulation-862 Tablet prepared by direct compression method] and [Formulation-872—Tablet prepared by spray-drying method] that were screened through dog clamp study indicated that formulation-872 prepared by the spray drying process exhibited comparatively consistent levels of drug absorption and resultant glucose infusion rate without loss of stability or biological activity affording a process of preparing a much economical, commercially viable and scalable method of manufacturing cation-insulin compound conjugate compositions.

TABLE 8

| Time | 862 | | 872 | |
|---|---|---|---|---|
| | Plasma Insulin | SEM | Plasma Insulin | SEM |
| 60 | 8.2 | 1.5 | 6.0 | 1.1 |
| 80 | 7.0 | 1.4 | 5.8 | 1.5 |
| 85 | 21.2 | 6.2 | 22.5 | 12.4 |
| 90 | 48.5 | 15.1 | 53.7 | 8.5 |
| 100 | 52.4 | 18.1 | 46.0 | 18.4 |
| 110 | 39.5 | 25.7 | 35.7 | 5.4 |
| 125 | 44.3 | 39.0 | 14.3 | 1.5 |
| 170 | 30.7 | 29.1 | 10.8 | 2.5 |
| 200 | 17.0 | 12.8 | 10.8 | 4.0 |
| 205 | 26.2 | 15.9 | 11.4 | 2.2 |
| 210 | 54.6 | 32.3 | 30.8 | 20.8 |
| 220 | 49.7 | 23.6 | 70.7 | 83.5 |
| 230 | 15.0 | 6.2 | 76.8 | 76.4 |
| 245 | 9.7 | 1.1 | 47.9 | 57.8 |
| 290 | 8.5 | 3.5 | 8.0 | 4.1 |
| 320 | 6.8 | 0.5 | 8.2 | 3.0 |

TABLE 9

| Time | 862 | | 872 | |
|---|---|---|---|---|
| | GIR | SEM | GIR | SEM |
| 60 | 0.00 | 0.00 | 0.00 | 0.00 |
| 80 | 0.00 | 0.00 | 0.00 | 0.00 |
| 85 | 0.00 | 0.00 | 0.00 | 0.00 |
| 90 | 0.00 | 0.00 | 0.00 | 0.00 |
| 100 | 3.20 | 0.86 | 2.52 | 1.14 |
| 110 | 2.49 | 1.03 | 4.72 | 1.04 |
| 125 | 1.72 | 1.58 | 1.02 | 0.02 |
| 170 | 2.82 | 2.87 | 0.00 | 0.00 |
| 200 | 1.92 | 2.16 | 0.00 | 0.00 |
| 205 | 0.05 | 0.06 | 0.00 | 0.00 |
| 210 | 0.46 | 0.56 | 0.00 | 0.00 |
| 220 | 2.16 | 1.41 | 1.52 | 0.68 |
| 230 | 1.95 | 1.74 | 4.90 | 1.75 |
| 245 | 2.05 | 1.16 | 4.80 | 6.78 |
| 290 | 0.43 | 0.41 | 1.03 | 1.46 |
| 320 | 0.43 | 0.41 | 0.35 | 0.49 |

TABLE 10

| Time | 862 | | 872 | |
|---|---|---|---|---|
| | Plasma glucose | SEM | Plasma glucose | SEM |
| 60 | 111.3 | 1.8 | 106.5 | 2.1 |
| 80 | 108.8 | 2.0 | 106.0 | 1.4 |
| 85 | 108.5 | 2.2 | 105.0 | 1.4 |
| 90 | 106.8 | 2.6 | 102.0 | 1.4 |
| 100 | 109.5 | 5.3 | 99.5 | 4.9 |
| 110 | 110.8 | 2.7 | 111.5 | 3.5 |
| 125 | 109.8 | 1.6 | 105.5 | 2.1 |
| 170 | 108.8 | 2.4 | 107.5 | 2.1 |
| 200 | 107.8 | 1.8 | 106.5 | 0.7 |
| 205 | 106.3 | 2.5 | 104.5 | 0.7 |
| 210 | 103.3 | 3.9 | 103.5 | 0.7 |
| 220 | 106.3 | 4.7 | 99.0 | 1.4 |
| 230 | 105.7 | 3.5 | 112.0 | 19.8 |
| 245 | 111.3 | 4.5 | 102.5 | 0.7 |
| 290 | 110.3 | 4.1 | 106.5 | 3.5 |
| 320 | 107.3 | 1.1 | 103.5 | 2.1 |

Example 12

Overnight dialyzed DS formulated as Insugen® and IN105, in 10 mM Tris, pH 8, were provided with the concentrations determined by HPLC quantitation.

TABLE 11

Table 11: Dialyzed Insulin concentrations used for the mitogenic assay study

| | INSULIN SAMPLES | | |
|---|---|---|---|
| | Insugen | IN-105 | HIM-2 |
| CONCENTRATION mg/ml | 2.84 | 2.65 | 20 |

3T3-A31 cells were obtained from ATCC (mouse fibroblast, ATCC CCL-163). Dulbecco's Modified Eagles Medium (DMEM), Heat Inactivated Fetal Bovine Serum (FBS) and Alamar Blue dye were procured from Invitrogen. IGF1 and 1M HEPES solution was obtained from Sigma Aldrich. 3T3-A31 cells were maintained in 10 mM HEPES-buffered DMEM supplemented with 10% FBS under humidified conditions at 37° C. in an atmosphere of 5% CO2. For the assay, 3T3-A31 cells were trypsinized with 0.25% trypsin-EDTA. The cell number was counted by hemocytometer using trypan blue staining. 10,000 cells per well were seeded in 10 mM HEPES buffered DMEM supplemented with 0.5% FBS in 96 well plates. Various concentrations of respective insulin were added in triplicates in the wells. After 20 hours of culture with the various concentrations of growth factors, Alamar Blue dye (10% v/v) was added and the plates were further incubated for additional 4 hours at 37° C. incubator. Fluorescence (Excitation wavelength=530 nm; Emission wavelength=590 nm) was measured using a 96 well plate reader.

TABLE 12

Mitogenic potency ratio comparison of Insugen versus IN-105 versus HIM-2 obtained from PLA analysis using 4 points in a linear range.

| INSUGEN | IN-105 | HIM-2 |
|---------|--------|-------|
| 1 | 0.237 | 0.044 |
| 1 | 0.256 | 0.021 |
| 1 | 0.286 | 0.048 |
| Average | 0.259 ± 0.020 | 0.0376 ± 0.020 |

Example 13

Overnight dialyzed DS formulated as Insugen® and IN105 in 10 mM Tris, pH 8 with the concentrations determined by HPLC quantitation is provided in TABLE 13.

TABLE 13

Dialyzed concentrations used for the metabolic study.

| | INSULIN SAMPLES | | |
|---|---|---|---|
| | Insugen | IN-105 | HIM-2 |
| CONCENTRATION mg/ml | 2.84 | 2.65 | 20 |

3T3-L1 cells were obtained from ATCC. Dulbecco's Modified Eagles Medium (DMEM), Heat Inactivated Fetal Bovine Serum (FBS), Penicillin-Streptomycin solution (10×) and 1M HEPES solution were procured from Invitrogen. Dexamethasone, Isobutyl methyl xanthine, 4-amino antipyrine, N-ethyl N-sulfopropyl m-toluidine and Glucose oxidase/peroxidase reagent were obtained from Sigma Aldrich.

3T3-L1 cells were maintained in 10 mM HEPES-buffered DMEM supplemented with 10% FBS, 100 U/100 µg Penicillin/Streptomycin (maintenance medium) under humidified conditions at 37° C. in an atmosphere of 5% CO2. For performing the metabolic assay, 3T3-L1 cells had to be differentiated to adipocytes. 3T3-L1 cells were trypsinized with 0.25% trypsin-EDTA. The cell number was counted by hemocytometer using trypan blue staining. 25,000 cells per well were seeded in maintenance medium in 96 well plates. The cells were allowed to attain confluency for the next 2 days. On day 3 the cells were replaced with differentiation medium (0.5 mM Dexamethasone and 0.25 µM Isobutyl methyl xanthine in maintenance medium) for additional four days. On day 7 the differentiation media was replaced back to maintenance media for three days. On day 9 the cells were washed with 1×PBS and various concentrations of respective insulin prepared in 15 mL centrifuge tubes in Low Glucose Medium assay buffer supplemented with 0.5% FBS, 2 mM L-glutamine and 1× Pen-Strep. The dilutions were added in triplicates in the wells. After 22 hours of culture with the various concentrations of Insulin, the 96 well plates were removed from the incubator for glucose estimation. The glucose was estimated by the help of GOPOD reagent which convert the glucose in the medium to gluconic acid and hydrogen peroxide. The hydrogen peroxide formed reacts with the substrate (4-amino antipyrine and N-ethyl N-sulfopropyl m-toluidine) to give a violet colored product which can be read at 550 nm wavelength. Metabolic activity calculations: For data representation % glucose left in the medium was measured by considering the value of "no insulin" as 100%.

The results of this assay indicated that the metabolic potencies of both Insugen®, IN105 and HIM-2 are similar and the potencies are within the acceptable limits (0.8-1.2) of the PLA analysis thereby establishing that Insugen and IN-105 are metabolically equipotent as represented in FIG. 14. FIG. 14 shows that the metabolic potency of Insugen® versus IN105 and Insugen® versus HIM-2 is same. The metabolic potency ratio of Insugen® to IN105 was found to be 1.166 and Insugen® to HIM-2 was found to be 1.149. The data represented Mean±SEM of triplicate determinations of an experiment FIG. 15 shows the parallelism and linearity of the bioassay across various concentrations of Insugen® and IN105 determined by the PLA software. The data represents average±SEM of triplicate values of an experiment.

TABLE 14

Metabolic potency ration comparison of Insugen versus IN-105 versus HIM-2 obtained from PLA analysis using 4 points in a linear range.

| INSUGEN | IN-105 | HIM-2 |
|---------|--------|-------|
| 1 | 1.121 | 1.19 |
| 1 | 1.2 | 1.104 |
| 1 | 1.179 | 1.153 |
| Average | 1.166 ± 0.041 | 1.149 ± 0.043 |

Example 14

The various insulin vials were clarified using glacial acetic acid (pH ~3.4). The clarified solution was then loaded on the C8 silica reverse phase column and separated using a gradient elution with 250 mM acetic acid and 100% ethanol. Fractions were collected during elution, and were pooled based on greater than or equal to 99% purity. This elution pool was dialyzed for 15 hrs. Using a 1 KD cut off membrane against 10 mM Tris, pH 8.0. Finally, dialysed Zn free and excipient free insulin, obtained at pH 8.0, was analyzed by analytical RP-HPLC. Overnight dialyzed DS Zinc free formulated as Insugen®, IN105 and HIM-2 in 10 mM Tris, pH 8 with the concentrations determined by HPLC quantitation is provided in TABLE 15.

TABLE 15

| | INSULIN SAMPLES | | |
|---|---|---|---|
| | Insugen | IN-105 | HIM-2 |
| CONCENTRATION mg/ml | 0.82 | 1.38 | 3.4 |

HepG2 cells were obtained from ATCC (ATCC Catalogue No. HB-8065). Dulbecco's Modified Eagle's medium (DMEM), Heat Inactivated Fetal Bovine Serum (FBS), 100× Penicillin-Streptomycin solution and 100×HEPES salt solution were procured from Invitrogen. Bovine serum albumin, Sodium hydroxide, Triton-X 100 and Sodium bicarbonate was obtained from Sigma Aldrich.

The radiolabeled recombinant human Insulin would be procured from Perkin Elmer with a specific radioactivity of 2200 Ci/mmole (Catalog No. NEX420)

HepG2 cells are maintained in 10 mM HEPES-buffered DMEM supplemented with 10% FBS and 1× Penicillin-Streptomycin solution under humidified conditions at 37° C. in an atmosphere of 5% CO2. For the assay, HepG2 cells are trypsinized and seeded at a density of 400,000 cells per well of a 24 well plate. After 3 days of incubation the cells are used to perform the radio-ligand binding assays (1, 2).

Prior to performing the assay the media is removed and the cells are washed twice with the Binding buffer (DMEM, 2.2 mg/ml Sodium bicarbonate, 1 mg/ml Bovine Serum albumin and 50 mM HEPES) to remove any traces of growth factors present in the medium. The competitive binding experiments are set up in duplicates using the fixed amount of radioligand (0.325 nM) and varying concentrations of cold Insulin drug substance (from 10-12 M to 10-7 M). The final reaction volume is made to 1 ml. The plates are then incubated at 15° C. overnight with shaker set at 100 rpm (2). The following day all the media from the wells are discarded and each well is washed twice with ice-cold binding buffer.

Each well received 1 ml of solubilization reagent (0.5 M Sodium hydroxide, 0.5% Triton-X 100). The solubilized cells are transferred to a Radioimmunoassay tube and the bound radioactivity was read in a gamma counter (Stratec BioMedical Systems, Germany) The instrument is calibrated and found to have an efficiency of 80%.

Binding Affinity calculations: For normalization of the Counts per minute (CPM values) at various concentrations of insulin used, percentage binding was calculated using the following equation;

% Bound=(CPMsample−CPMblank)/(CPMcontrol−CPMblank)×100

Where CPMcontrol is the average CPM of the wells which contained cells with radiolabeled Insulin without any cold Insulin added, CPMblank is the average CPM of the wells which did not contain radiolabeled Insulin as well as cold insulin and CPMsample was the average CPM of the wells which contained radiolabeled Insulin as well as varying concentrations of cold Insulin.

TABLE 16

Comparison of the Binding Affinities in terms of EC50 values with their 95% Confidence Interval.

|  | EC50 (M) | 95% CI for EC50 (M) |
|---|---|---|
| Insugen (R) | $1.246 \times 10^{-10}$ | $(1.005, 1.544) \times 10^{-10}$ |
| IN105 | $1.185 \times 10^{-10}$ | $(0.863, 1.626) \times 10^{-10}$ |
| HIM-2 | $1.157 \times 10^{-10}$ | $(0.896, 1.495) \times 10^{-10}$ |

The above description and examples have been given for ease of understanding only. No unnecessary limitations should be understood there from, as modifications will be obvious to those skilled in the art who will recognize that the invention can be practiced with modifications and variations within the spirit of the appended claims.

The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

We claim:

1. An orally administrable tablet pharmaceutical composition of IN-105 comprising about 0.01%-20% w/w of IN-105 which is an insulin compound conjugate, about 10%-60% w/w of saturated or unsaturated $C_4$-$C_{12}$ fatty acids, fatty acid esters or salts thereof, 10%-60% w/w of a diluent, 1%-20% w/w of disintegrant, 0.5% w/w of a lubricant and optionally including binders, plasticizers, permeation enhancers and solubilizers, wherein the lubricant is magnesium stearate.

2. The pharmaceutical composition of claim 1, wherein the fatty acid component is capric acid and/or lauric acid or salts thereof.

3. The pharmaceutical composition of claim 1, wherein the binder is selected from the group consisting of polyvinylpyrrolidone, carboxymethylcellulose, methylcellulose, starch, gelatin, sugars, natural gums, synthetic gums and combinations thereof.

4. The pharmaceutical composition of claim 1, wherein the diluents is selected from the group consisting of calcium salts, cellulose, cellulose derivatives, palatinose, organic acids, sugar, sugar alcohols, pectate salts and combinations thereof.

5. The pharmaceutical composition of claim 1, wherein the disintegrant is selected from the group consisting of cross-linked polyvinylpyrrolidone, carboxymethylcellulose, methyl cellulose, cation-exchange resins, alginic acid, guar gum and their combinations thereof.

6. The pharmaceutical composition of claim 1, wherein the permeation enhancer is selected from the group consisting of sodium lauryl sulfate, sodium laurate, palmitoyl carnitine, phosphatidylcholine, cyclodextrin, cyclodextrin derivatives, carnithine, carnithine derivatives, mucoadhesive polymers, zonula occludins toxin, bile salts, fatty acids and combinations thereof.

7. The pharmaceutical composition of claim 1, wherein the plasticizer is selected from the group consisting of polyethyleneglycol, propylene glycol, acetyl citrate, triacetin, acetylated monoglyceride, rape oil, olive oil, sesame oil, acetyltriethyl citrate, glycerin sorbitol, diethyloxalate, diethylmalate, diethylfumarate, dibutylsuccinate, dibutyl phthalate, dioctylphthalate, dibutylsebacate, triethylcitrate, tributylcitrate, glyceroltributyrate, glyceryl triacetate and mixtures thereof.

8. A process for manufacturing an orally administrable solid pharmaceutical composition of IN 105, comprising about 0.01%-20% w/w of IN-105, about 10%-60% w/w of saturated or unsaturated C4-C12 fatty acids, fatty acid esters or salts thereof, 10%-60% w/w of a diluent, 1%-20% w/w of disintegrant, 0.5% w/w of a lubricant and optionally including binders, plasticizers, permeation enhancers and solubilizers, wherein the lubricant is magnesium stearate, the method comprising the steps of:
 a. grinding a suitable saturated or unsaturated C4-C12 fatty acids and/or salts of such fatty acid;
 b. granulating the resulting fatty acid obtained from step (a) with an organic solvent;
 c. air-drying the granules obtained from step (b);
 d. rasping the dried granules through a mesh to obtain granules of desired particle size;
 e. blending the fatty acid granules with the cation-insulin conjugate complex with the other excipients; and
 f. compressing the blended mixture for tablet formation.

9. A process for manufacturing an orally administrable tablet pharmaceutical composition of IN105, comprising about 0.01%-20% w/w of IN-105, about 10%-60% w/w of saturated or unsaturated C4-C12 fatty acids, fatty acid esters or salts thereof, 0.01%-5% of binder, 10%-60% w/w of a diluent, 1%-20% w/w of disintegrant, 0.5% w/w of a lubricant and optionally including binders, plasticizers, permeation enhancers and solubilizers, wherein the lubricant is magnesium stearate, the method comprising the steps of:
   a. grinding suitable saturated or unsaturated C4-C12 fatty acids and/or salts of such fatty acid and a binder;
   b. suspending the cation-insulin conjugate complex in an organic solvent using the binder to form a wet mass;
   c. granulation of the components obtained from step (b) using the binder to form dried granules;
   d. rasping the dried granules of step (c);
   e. blending the dried granules with other excipients; and
   f. compressing the blended mixture for tablet formation.

10. A process according to claim 8 or 9, wherein the organic solvent used is selected from the group comprising isopropanol, acetone, methyl alcohol, methyl isobutyl ketone, chloroform, 1-propanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

11. A 5-500 mg tablet of an orally administrable tablet pharmaceutical composition according to claim 1.

12. A tablet according to claim 11, being a 50 mg tablet, a 100 mg tablet, a 150 mg tablet, a 200 mg tablet or a 250 mg tablet.

13. A dose of the orally administrable tablet pharmaceutical composition of claim 1, to achieve a maximum control of post prandial blood glucose concentration in diabetic patients within 5-60 minutes post-administration.

14. The orally administrable tablet pharmaceutical composition according to claim 1, which produces a lowered serum glucose in human patients by at least 5% within 120 minutes post oral administration.

15. A stable orally administrable tablet pharmaceutical composition of IN-105 according to claim 1, characterized in that said composition remains stable over exposure to conditions selected from the group consisting of
   a. temperature range of about 2-40° C.; and
   b. 25° C.±2° C./60%±5% relative humidity (RH), 30° C.±2° C./65%±5% relative humidity, 40° C.±2° C./75%±5% relative humidity for over a period of at least 6 months.

16. The stable orally administrable tablet pharmaceutical composition according to claim 15, characterized in that impurities do not increase by more than 5% when compared to the impurity levels at the time of manufacture.

17. The stable orally administrable tablet pharmaceutical composition according to claim 15, characterized in that impurities do not increase by more than 10% when compared to the impurity levels at the time of manufacture.

18. The stable orally administrable tablet pharmaceutical composition according to claim 15, characterized in that an assay of said compound in the composition does not decrease by more than 10%.

19. The stable orally administrable tablet pharmaceutical composition according to claim 1, characterized in that a dissolution profile is at least 75% at any said time interval.

20. The stable orally administrable tablet pharmaceutical composition according to claim 19, wherein a time interval ranges for a period over 2 years.

21. The stable orally administrable tablet pharmaceutical composition according to claim 15, characterized in that a difference between a hardness profile is no more than 1 kg/cm$^2$ when compared to a hardness profile at the time of manufacture.

22. The stable orally administrable tablet pharmaceutical composition according to claim 15, characterized in that at least 95%±2% of the composition remains undegraded over exposure to conditions selected from the group consisting of:
   (a) temperature range of about 2-8° C. or 25° C.-40° C.; and
   (b) 25° C.±2° C./60%±5% relative humidity (RH), 30° C.±2° C./65%±5% relative humidity, 40° C.±2° C./75%±5% relative humidity for over a period of at least 6 months.

23. The stable orally administrable tablet pharmaceutical composition according to claim 15, characterized in that at least 90%±2% of the composition remains undegraded over exposure to conditions selected from the group consisting of:
   a. temperature range of about 2-8° C. or 25° C.-40° C.; and
   b. 25° C.±2° C./60%±5% relative humidity (RH), 30° C.±2° C./65%±5% relative humidity, 40° C.±2° C./75%±5% relative humidity for over a period of at least 6 months.

24. The orally administrable tablet pharmaceutical composition of claim 2, wherein the fatty acid component is sodium caprate.

25. The orally administrable tablet pharmaceutical composition of claim 3, wherein the binder is polyvinylpyrrolidone.

26. The orally administrable tablet pharmaceutical composition of claim 4, wherein the diluent is mannitol.

27. The orally administrable tablet pharmaceutical composition of claim 1, wherein the diluent is mannitol, the disintegrant is polyvinylpyrrolidone and the fatty acid is sodium caprate.

28. The orally administrable tablet pharmaceutical composition of claim 6, wherein the permeation enhancer is sodium lauryl sulphate or beta-cyclodextrin.

29. The orally administrable tablet pharmaceutical composition of claim 1, wherein IN-105 is an insulin molecule conjugated at the epsilon amino acid Lysine at position B29 of the insulin B-chain with an amphiphilic oligomer of structural formula $CH_3O(C_4H_2O)_3CH_2CH_2COOH$.

\* \* \* \* \*